United States Patent
Locke et al.

(10) Patent No.: US 12,329,895 B2
(45) Date of Patent: Jun. 17, 2025

(54) CUSTOMIZABLE DRESSING WITH INTEGRATED BRIDGE

(71) Applicant: KCI Manufacturing Unlimited Company, Westmeath (IE)

(72) Inventors: Christopher Brian Locke, Bournemouth (GB); James A. Luckemeyer, San Antonio, TX (US)

(73) Assignee: KCI Manufacturing Unlimited Company, Westmeath (IE)

(*) Notice: Subject to any disclaimer, the term of this patent is extended or adjusted under 35 U.S.C. 154(b) by 87 days.

(21) Appl. No.: 18/033,036

(22) PCT Filed: Sep. 23, 2021

(86) PCT No.: PCT/IB2021/058702
§ 371 (c)(1),
(2) Date: Apr. 20, 2023

(87) PCT Pub. No.: WO2022/084771
PCT Pub. Date: Apr. 28, 2022

(65) Prior Publication Data
US 2023/0390481 A1    Dec. 7, 2023

Related U.S. Application Data

(60) Provisional application No. 63/094,778, filed on Oct. 21, 2020.

(51) Int. Cl.
*A61M 1/00*    (2006.01)
(52) U.S. Cl.
CPC .................................. *A61M 1/913* (2021.05)

(58) Field of Classification Search
CPC ...... A61M 1/912; A61M 1/913; A61M 1/915; A61M 1/916; A61M 1/917; A61M 1/918;
(Continued)

(56) References Cited

U.S. PATENT DOCUMENTS

| | | |
|---|---|---|
| 1,355,846 A | 10/1920 | Rannells |
| 2,547,758 A | 4/1951 | Keeling |

(Continued)

FOREIGN PATENT DOCUMENTS

| | | |
|---|---|---|
| AU | 550575 B2 | 3/1986 |
| AU | 745271 B2 | 3/2002 |

(Continued)

OTHER PUBLICATIONS

International Search Report and Written Opinion for Corresponding Application No. PCT/IB2021/058702, mailed Dec. 1, 2021.

(Continued)

*Primary Examiner* — Sarah Al Hashimi
*Assistant Examiner* — Arjuna P Chatrathi

(57) ABSTRACT

A dressing for treating a tissue site with negative pressure may comprise a manifold layer having a first surface configured to face the tissue site, a second surface opposite the first surface, and a thickness extending between the first surface and the second surface. The manifold layer may comprise a tissue portion and a bridge portion. The bridge portion may be coupled to the tissue portion and may comprise a distal end configured to be extended away from the tissue portion. The dressing may also comprise a flexible drape configured to form a sealed space including the manifold layer at the tissue site.

27 Claims, 10 Drawing Sheets

(58) Field of Classification Search
CPC ............ A61F 13/05; A61F 2013/00533; A61F 2013/00812; A61F 2013/49063; A61F 2013/49066
See application file for complete search history.

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,478,308 A * | 12/1995 | Cartmell ............... A61F 15/001 602/42 |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 5,885,237 A * | 3/1999 | Kadash ............. A61F 13/01042 602/56 |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,398,614 B2 | 3/2013 | Blott et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,679,081 B2 | 3/2014 | Heagle et al. |
| 8,834,451 B2 | 9/2014 | Blott et al. |
| 8,926,592 B2 | 1/2015 | Blott et al. |
| 9,017,302 B2 | 4/2015 | Vitaris et al. |
| 9,198,801 B2 | 12/2015 | Weston |
| 9,211,365 B2 | 12/2015 | Weston |
| 9,289,542 B2 | 3/2016 | Blott et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2006/0241689 A1 * | 10/2006 | Leiboff ................. A61M 27/00 606/213 |
| 2010/0087767 A1 * | 4/2010 | McNeil ................. A61M 1/915 602/42 |
| 2010/0262090 A1 * | 10/2010 | Riesinger .......... A61F 13/01017 604/374 |
| 2010/0324510 A1 * | 12/2010 | Andresen ................ A61F 13/05 604/319 |
| 2014/0163491 A1 | 6/2014 | Schuessler et al. |
| 2014/0343517 A1 * | 11/2014 | Jameson ............... A61M 1/915 604/319 |
| 2015/0080788 A1 | 3/2015 | Blott et al. |
| 2015/0141941 A1 | 5/2015 | Allen et al. |
| 2016/0022500 A1 * | 1/2016 | Tumey ................. A61M 1/915 604/319 |
| 2016/0144084 A1 * | 5/2016 | Collinson ............... A61F 13/05 604/319 |

(56) References Cited

U.S. PATENT DOCUMENTS

| | | | | |
|---|---|---|---|---|
| 2018/0333522 | A1* | 11/2018 | Pratt | A61F 13/148 |
| 2019/0350764 | A1* | 11/2019 | Zochowski | A61M 1/67 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2195255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/20041 A1 | 9/1994 |
| WO | 96/05873 A1 | 2/1996 |
| WO | 97/18007 A1 | 5/1997 |
| WO | 99/13793 A1 | 3/1999 |
| WO | 2016/126444 A1 | 8/2016 |
| WO | 2019/083979 A1 | 5/2019 |
| WO | 2020/033351 A1 | 2/2020 |

OTHER PUBLICATIONS

Louis C. Argenta, MD and Michael J. Morykwas, Phd; Vacuum-Assisted Closure: A New Method for Wound Control and Treatment: Clinical Experience; Annals of Plastic Surgery; vol. 38, No. 6, Jun. 1997; pp. 563-576.
Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp . 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, p. 24.
Egnell Minor: Addition to the Users Manual Concerning Overflow Protection—Concerns all Egnell Pumps, Feb. 3, 1983, p. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, The Use of Hypermia in the Postoperative Treatment of Lesions of the Extremities and Thorax, Journal of the American Medical Association 64 (1915), pp. 1548-1549.

(56) References Cited

OTHER PUBLICATIONS

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians; Jul. 2007.

\* cited by examiner

CUSTOMIZABLE DRESSING WITH INTEGRATED BRIDGE

CROSS-REFERENCE TO RELATED APPLICATIONS

This application claims the benefit of priority to U.S. Provisional Application No. 63/094,778, filed on Oct. 21, 2020, which is incorporated herein by reference in its entirety.

TECHNICAL FIELD

The invention set forth in the appended claims relates generally to tissue treatment systems and more particularly, but without limitation, to dressings for tissue treatment with negative pressure and methods of using the dressings for tissue treatment with negative pressure.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

While the clinical benefits of negative-pressure therapy are widely known, improvements to therapy systems, components, and processes may benefit healthcare providers and patients.

BRIEF SUMMARY

New and useful systems, apparatuses, and methods for treating tissue in a negative-pressure therapy environment are set forth in the appended claims. Illustrative embodiments are also provided to enable a person skilled in the art to make and use the claimed subject matter.

For example, in some embodiments, a dressing for treating tissue may be utilized to provide negative-pressure therapy to relatively challenging tissue sites. Such tissue sites may include, without limitation, those tissue sites having an anatomy, position, geometry, and/or dimensions that may cause difficulty in providing an effective and reliable route of fluid communication between the tissue site and a source of negative pressure. Challenging tissue sites might include an elbow or heel, for example, those tissue sites where it may be difficult to provide for attachment of a fluid conductor. More generally, some embodiments may comprise a dressing configured to provide for attachment for a fluid conductor at a location spaced away from the tissue site receiving negative pressure therapy.

In some embodiments, a dressing for treating a tissue site with negative pressure may comprise a manifold layer having a first surface configured to face the tissue site, a second surface opposite the first surface, and a thickness extending between the first surface and the second surface. The manifold layer may comprise a tissue portion and a bridge portion. The bridge portion may be coupled to the tissue portion and may comprise a distal end configured to be extended away from the tissue portion. For example, the bridge portion may provide for attachment for a fluid conductor at a location spaced away from the tissue site receiving negative pressure therapy, for example, by providing a route of fluid communication between the tissue portion and the site of attachment for the fluid conductor. The dressing may also comprise a flexible drape configured to form a sealed space including the manifold layer at the tissue site.

In some embodiments, a system for treating a tissue site may comprise a dressing. The dressing may comprise a manifold layer having a first surface configured to face the tissue site, a second surface opposite the first surface, and a thickness extending between the first surface and the second surface. The manifold layer may comprise a tissue portion and a bridge portion. The bridge portion may be coupled to the tissue portion and may comprise a distal end configured to be extended away from the tissue portion. The dressing may also comprise a flexible drape configured to form a sealed space including the manifold layer at the tissue site. The system may also comprise a negative-pressure source fluidly coupled to the dressing.

In some embodiments, a method is for treating a tissue site with negative pressure with a dressing. The dressing may comprise a manifold layer having a first surface configured to face the tissue site, a second surface opposite the first surface, and a thickness extending between the first surface and the second surface. The manifold layer may comprise a tissue portion and a bridge portion. The bridge portion may be coupled to the tissue portion and may comprise a distal end configured to be extended away from the tissue portion. The dressing may also comprise a flexible drape configured to form a sealed space including the manifold layer at the tissue site. The method may comprise extending the bridge portion of the manifold layer of the dressing away from the tissue portion of the dressing. The method may also comprise positioning the manifold layer with respect to the tissue site such that the tissue portion is adjacent the tissue site and the bridge portion extends away from the tissue site. The method may also comprise sealing the manifold layer to epidermis adjacent to the tissue site. The method may also comprise fluidly coupling the dressing to a negative-pressure source via the bridge portion. The method may also comprise applying negative pressure from the negative-pressure source to the dressing.

DESCRIPTION OF EXAMPLE EMBODIMENTS

The following description of example embodiments provides information that enables a person skilled in the art to make and use the subject matter set forth in the appended claims, and may omit certain details already well-known in the art. The following detailed description is, therefore, to be taken as illustrative and not limiting.

Figure 1:
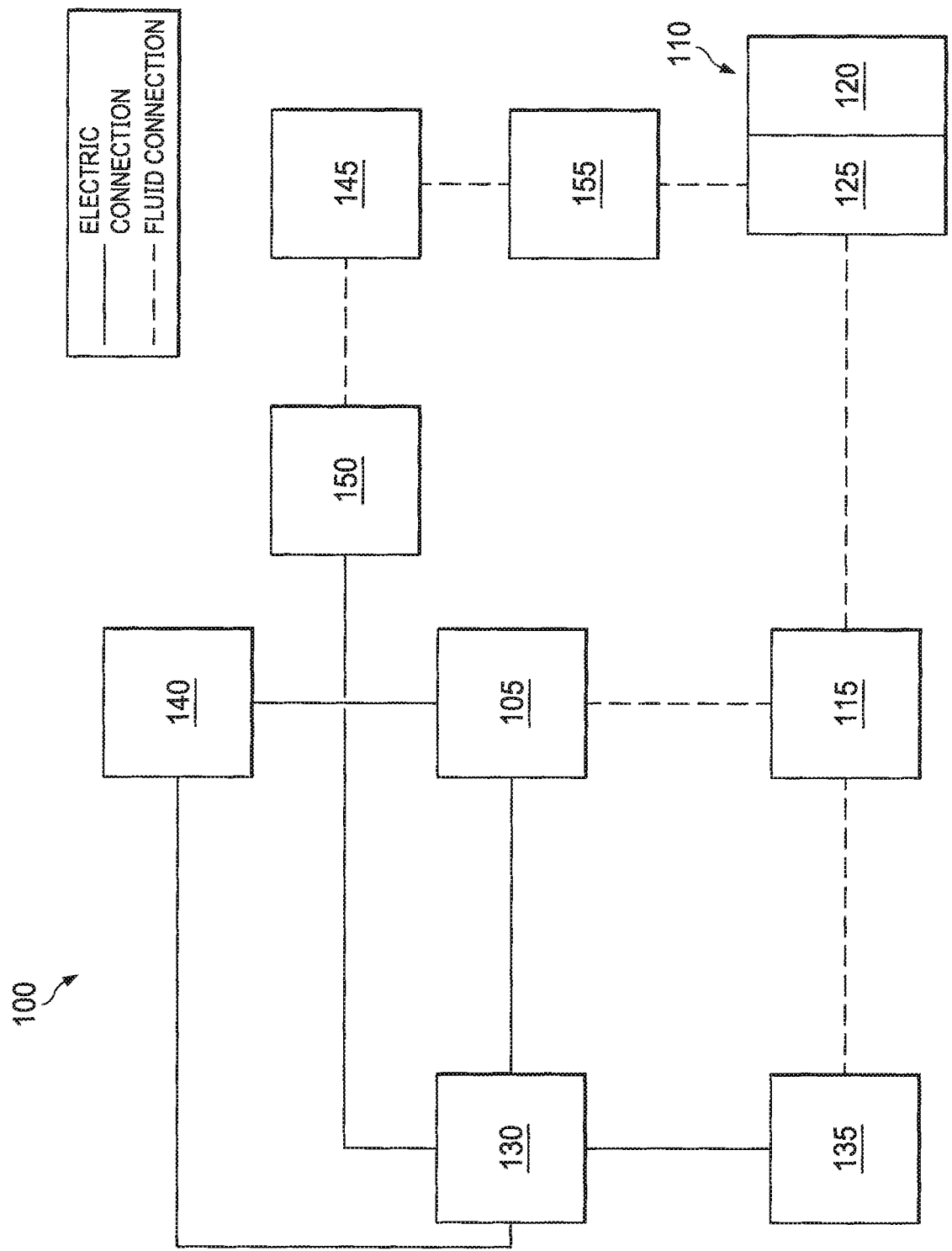
FIG. 1 is a block diagram of an example embodiment of a therapy system and a dressing that can provide tissue treatment in accordance with this specification.

FIG. 1 is a block diagram of an example embodiment of a therapy system 100 that can provide negative-pressure therapy with instillation of topical treatment solutions to a tissue site in accordance with this specification.

The term "tissue site" in this context broadly refers to a wound, defect, or other treatment target located on or within tissue, including, but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, negative pressure may be applied to a tissue site to grow additional tissue that may be harvested and transplanted.

The therapy system 100 may include a source or supply of negative pressure, such as a negative-pressure source 105, and one or more distribution components. A distribution component is preferably detachable and may be disposable, reusable, or recyclable. A dressing, such as a dressing 110, and a fluid container, such as a container 115, are examples of distribution components that may be associated with some examples of the therapy system 100. As illustrated in the example of FIG. 1, the dressing 110 may comprise a tissue interface 120, a cover 125, or both in some embodiments.

A fluid conductor is another illustrative example of a distribution component. A "fluid conductor," in this context, broadly includes a tube, pipe, hose, conduit, or other structure with one or more lumina or open pathways adapted to convey a fluid between two ends. Typically, a tube is an elongated, cylindrical structure with some flexibility, but the geometry and rigidity may vary. Moreover, some fluid conductors may be molded into or otherwise integrally combined with other components. Distribution components may also include or comprise interfaces or fluid ports to facilitate coupling and de-coupling other components. In some embodiments, for example, a dressing interface may facilitate coupling a fluid conductor to the dressing 110. For example, such a dressing interface may be a SENSA-T.R.A.C.™ Pad available from Kinetic Concepts, Inc. of San Antonio, Texas.

The therapy system 100 may also include a regulator or controller, such as a controller 130. Additionally, the therapy system 100 may include sensors to measure operating parameters and provide feedback signals to the controller 130 indicative of the operating parameters. As illustrated in FIG. 1, for example, the therapy system 100 may include a first sensor 135 and a second sensor 140 coupled to the controller 130.

The therapy system 100 may also include a source of instillation solution. For example, a solution source 145 may be fluidly coupled to the dressing 110, as illustrated in the example embodiment of FIG. 1. The solution source 145 may be fluidly coupled to a positive-pressure source such as a positive-pressure source 150, a negative-pressure source such as the negative-pressure source 105, or both in some embodiments. A regulator, such as an instillation regulator 155, may also be fluidly coupled to the solution source 145 and the dressing 110 to ensure proper dosage of instillation solution (e.g. saline) to a tissue site. For example, the instillation regulator 155 may comprise a piston that can be pneumatically actuated by the negative-pressure source 105 to draw instillation solution from the solution source during a negative-pressure interval and to instill the solution to the dressing 110 during a venting interval. Additionally or alternatively, the controller 130 may be coupled to the negative-pressure source 105, the positive-pressure source 150, or both, to control dosage of instillation solution to a tissue site. In some embodiments, the instillation regulator 155 may also be fluidly coupled to the negative-pressure source 105 through the dressing 110, as illustrated in the example of FIG. 1.

Some components of the therapy system 100 may be housed within or used in conjunction with other components, such as sensors, processing units, alarm indicators, memory, databases, software, display devices, or user interfaces that further facilitate therapy. For example, in some embodiments, the negative-pressure source 105 may be combined with the controller 130, the solution source 145, and other components into a therapy unit.

In general, components of the therapy system 100 may be coupled directly or indirectly. For example, the negative-pressure source 105 may be directly coupled to the container 115 and may be indirectly coupled to the dressing 110 through the container 115. Coupling may include fluid, mechanical, thermal, electrical, or chemical coupling (such as a chemical bond), or some combination of coupling in some contexts. For example, the negative-pressure source 105 may be electrically coupled to the controller 130 and may be fluidly coupled to one or more distribution components to provide a fluid path to a tissue site. In some embodiments, components may also be coupled by virtue of physical proximity, being integral to a single structure, or being formed from the same piece of material.

A negative-pressure supply, such as the negative-pressure source 105, may be a reservoir of air at a negative pressure or may be a manual or electrically-powered device, such as a vacuum pump, a suction pump, a wall suction port available at many healthcare facilities, or a micro-pump, for example. "Negative pressure" generally refers to a pressure less than a local ambient pressure, such as the ambient pressure in a local environment external to a sealed therapeutic environment. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. References to increases in negative pressure typically refer to a decrease in absolute pressure, while decreases in negative pressure typically refer to an increase in absolute pressure. While the amount and nature of negative pressure provided by the negative-pressure source 105 may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −50 mm Hg (−6.7 kPa) and −300 mm Hg (−39.9 kPa).

The container 115 is representative of a container, canister, pouch, or other storage component, which can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with negative-pressure therapy.

A controller, such as the controller 130, may be a microprocessor or computer programmed to operate one or more components of the therapy system 100, such as the negative-pressure source 105. In some embodiments, for example, the controller 130 may be a microcontroller, which generally comprises an integrated circuit containing a processor core and a memory programmed to directly or indirectly control one or more operating parameters of the therapy system 100. Operating parameters may include the power applied to the negative-pressure source 105, the pressure generated by the negative-pressure source 105, or the pressure distributed to the tissue interface 120, for example. The controller 130 is also preferably configured to receive one or more input signals, such as a feedback signal, and programmed to modify one or more operating parameters based on the input signals.

Sensors, such as the first sensor 135 and the second sensor 140, are generally known in the art as any apparatus operable to detect or measure a physical phenomenon or property, and generally provide a signal indicative of the phenomenon or property that is detected or measured. For example, the first sensor 135 and the second sensor 140 may be configured to measure one or more operating parameters of the therapy system 100. In some embodiments, the first sensor 135 may be a transducer configured to measure pressure in a pneumatic pathway and convert the measurement to a signal indicative of the pressure measured. In some embodiments, for example, the first sensor 135 may be a piezo-resistive strain gauge. The second sensor 140 may optionally measure operating parameters of the negative-pressure source 105, such as a voltage or current, in some embodiments. Preferably, the signals from the first sensor 135 and the second sensor 140 are suitable as an input signal to the controller 130, but some signal conditioning may be appropriate in some embodiments. For example, the signal may need to be filtered or amplified before it can be processed by the controller 130. Typically, the signal is an electrical signal, but may be represented in other forms, such as an optical signal.

The tissue interface 120 can be generally adapted to partially or fully contact a tissue site. The tissue interface 120 may take many forms, and may have many sizes, shapes, or thicknesses, depending on a variety of factors, such as the type of treatment being implemented or the nature and size of a tissue site. For example, the size and shape of the tissue interface 120 may be adapted to the contours of deep and irregular shaped tissue sites. Any or all of the surfaces of the tissue interface 120 may have an uneven, coarse, or jagged profile.

In some embodiments, the tissue interface 120 may include or be formed from a manifold. A manifold in this context may comprise a means for collecting or distributing fluid relative to a tissue site under pressure. For example, a manifold may be adapted to receive negative pressure from a source and distribute negative pressure through multiple apertures, which may have the effect of collecting fluid from across a tissue site and drawing the fluid toward the source. In some embodiments, the fluid path may be reversed or a secondary fluid path may be provided to facilitate delivering fluid, such as fluid from a source of instillation solution, across a tissue site.

The tissue interface 120 may include either hydrophobic or hydrophilic components. In an example in which the tissue interface 120 may be hydrophilic, the tissue interface 120 may also wick fluid away from a tissue site, while continuing to distribute negative pressure to the tissue site. The wicking properties of the tissue interface 120 may draw fluid away from a tissue site by capillary flow or other wicking mechanisms. An example of a hydrophilic material that may be suitable is a polyvinyl alcohol, open-cell foam such as V.A.C. WHITEFOAM™ dressing available from Kinetic Concepts, Inc. of San Antonio, Texas. Other hydrophilic foams may include those made from polyether. Other foams that may exhibit hydrophilic characteristics include hydrophobic foams that have been treated or coated to provide hydrophilicity.

In some embodiments, the tissue interface 120 may be include bioresorbable materials. Suitable bioresorbable materials may include, without limitation, a polymeric blend of polylactic acid (PLA) and polyglycolic acid (PGA). The polymeric blend may also include, without limitation, polycarbonates, polyfumarates, and capralactones. The tissue interface 120 may further serve as a scaffold for new cell-growth, or a scaffold material may be used in conjunction with the tissue interface 120 to promote cell-growth. A scaffold is generally a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

In some embodiments, the cover 125 may be a sealing layer comprising or formed from a soft, pliable material suitable for providing a fluid seal with a tissue site, and may have a substantially flat surface. The cover 125 may provide a bacterial barrier and protection from physical trauma. The cover 125 may also be constructed from a material that can reduce evaporative losses and provide a fluid seal between two components or two environments, such as between a therapeutic environment and a local external environment. The cover 125 may comprise or be formed from, for example, an elastomeric film or membrane that can provide a seal adequate to maintain a negative pressure at a tissue site for a given negative-pressure source. The cover 125 may have a high moisture-vapor transmission rate (MVTR) in some applications. For example, the MVTR may be at least 250 grams per square meter per twenty-four hours in some embodiments, measured using an upright cup technique according to ASTM E96/E96M Upright Cup Method at 38° C. and 10% relative humidity (RH). In some embodiments, an MVTR up to 5,000 grams per square meter per twenty-four hours may provide effective breathability and mechanical properties.

In some example embodiments, the cover 125 may be a polymer drape, such as a polyurethane film, that is permeable to water vapor but impermeable to liquid. Such drapes typically have a thickness in the range of 25-50 microns. For permeable materials, the permeability generally should be low enough that a desired negative pressure may be maintained. The cover 125 may comprise, for example, one or more of the following materials: polyurethane (PU), such as hydrophilic polyurethane; cellulosics; hydrophilic polyamides; polyvinyl alcohol; polyvinyl pyrrolidone; hydrophilic acrylics; silicones, such as hydrophilic silicone elastomers; natural rubbers; polyisoprene; styrene butadiene rubber; chloroprene rubber; polybutadiene; nitrile rubber; butyl rubber; ethylene propylene rubber; ethylene propylene diene monomer; chlorosulfonated polyethylene; polysulfide rubber; ethylene vinyl acetate (EVA); co-polyester; and polyether block polyamide copolymers. Such materials are commercially available as, for example, Tegaderm® drape, commercially available from 3M Company, Minneapolis Minnesota; polyurethane (PU) drape, commercially available from Avery Dennison Corporation, Pasadena, California; polyether block polyamide copolymer (PEBAX), for example, from Arkema S.A., Colombes, France; and Inspire 2301 and Inspire 2327 polyurethane films, commercially available from Exopack Advanced Coatings, Wrexham, United Kingdom. In some embodiments, the cover 125 may comprise Inspire 2301 having an MVTR (upright cup technique) of 2600 grams per square meter per twenty-four hours and a thickness of about 30 microns.

An attachment device may be used to attach the cover 125 to an attachment surface, such as undamaged epidermis, a gasket, or another cover. The attachment device may take many forms. For example, an attachment device may be a medically-acceptable, pressure-sensitive adhesive configured to bond the cover 125 to epidermis around a tissue site. In some embodiments, for example, some or all of the cover 125 may be coated with an adhesive, such as an acrylic adhesive, which may have a coating weight of about 25-65 grams per square meter (g.s.m.). Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

The solution source 145 may also be representative of a container, canister, pouch, bag, or other storage component, which can provide a solution for instillation therapy. Compositions of solutions may vary according to a prescribed therapy, but examples of solutions that may be suitable for some prescriptions include hypochlorite-based solutions, silver nitrate (0.5%), sulfur-based solutions, biguanides, cationic solutions, and isotonic solutions.

In operation, the tissue interface 120 may be placed within, over, on, or otherwise proximate to a tissue site. If the tissue site is a wound, for example, the tissue interface 120 may partially or completely fill the wound, or it may be placed over the wound. The cover 125 may be placed over the tissue interface 120 and sealed to an attachment surface near a tissue site. For example, the cover 125 may be sealed to undamaged epidermis peripheral to a tissue site. Thus, the dressing 110 can provide a sealed therapeutic environment proximate to a tissue site, substantially isolated from the external environment, and the negative-pressure source 105 can reduce pressure in the sealed therapeutic environment.

The process of reducing pressure may be described illustratively herein as "delivering," "distributing," or "generating" negative pressure, for example. In general, exudate and other fluid flow toward lower pressure along a fluid path. Thus, the term "downstream" typically refers to a location in a fluid path relatively closer to a source of negative pressure or further away from a source of positive pressure. Conversely, the term "upstream" refers to a location in a fluid path relatively further away from a source of negative pressure or closer to a source of positive pressure. Similarly, it may be convenient to describe certain features in terms of fluid "inlet" or "outlet" in such a frame of reference. This orientation is generally presumed for purposes of describing various features and components herein. However, the fluid path may also be reversed in some applications, such as by substituting a positive-pressure source for a negative-pressure source, and such a description should not be construed as limiting.

Negative pressure applied across the tissue site through the tissue interface 120 in the sealed therapeutic environment can induce macro-strain and micro-strain in the tissue site. Negative pressure can also remove exudate and other fluid from a tissue site, which can be collected in the container 115.

In some embodiments, the controller 130 may receive and process data from one or more sensors, such as the first sensor 135. The controller 130 may also control the operation of one or more components of the therapy system 100 to manage the pressure delivered to the tissue interface 120. In some embodiments, the controller 130 may include an input for receiving a desired target pressure and may be programmed for processing data relating to the setting and inputting of the target pressure to be applied to the tissue interface 120. In some example embodiments, the target pressure may be a fixed pressure value set by an operator as the target negative pressure desired for therapy at a tissue site and then provided as input to the controller 130. The target pressure may vary from tissue site to tissue site based on the type of tissue forming a tissue site, the type of injury or wound (if any), the medical condition of the patient, and the preference of the attending physician. After selecting a desired target pressure, the controller 130 can operate the negative-pressure source 105 in one or more control modes based on the target pressure and may receive feedback from one or more sensors to maintain the target pressure at the tissue interface 120.

Figure 2:
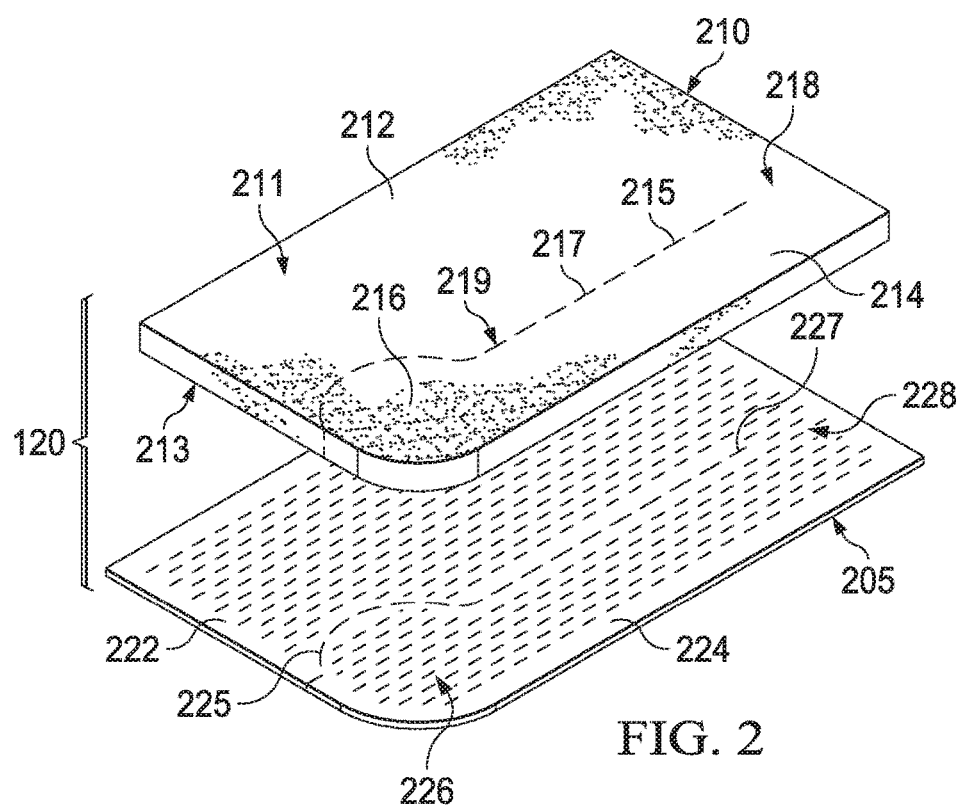
FIG. 2 is an exploded view of an example of a tissue interface, illustrating additional details that may be associated with some example embodiments of the therapy system and the dressing of FIG. 1.

FIG. 2 is an exploded view of an example of the tissue interface 120 of FIG. 1, illustrating additional details that may be associated with some embodiments in which the tissue interface 120 comprises more than one layer. In the example of FIG. 2, the tissue interface 120 comprises a manifold layer 210 and a fluid management layer 205. The manifold layer 210 may be disposed adjacent to the fluid management layer 205. For example, the manifold layer 210 and the fluid management layer 205 may be stacked so that the manifold layer 210 is in contact with the fluid management layer 205. In some embodiments, the manifold layer 210 and the fluid management layer 205 may also be bonded, for example, via an adhesive.

The manifold layer 210 may generally comprise a first surface 211, a second surface 213, and a thickness extending between the first surface 211 and the second surface 213. In some embodiments, the first surface and/or the second surface may be generally characterized as planar surfaces, for example, although not necessarily perfectly flat, being generally recognizable as flat or capable of being laid flat. For example, a planar surface may include minor undulations and/or deviations from a single geometric plane.

In some illustrative embodiments, the manifold layer 210 may comprise a plurality of pathways, which can be interconnected to improve distribution or collection of fluids. In some embodiments, the manifold layer 210 may comprise or be formed from a porous material having interconnected fluid pathways. For example, open-cell foam, reticulated foam, porous tissue collections, and other porous material such as gauze or felted mat generally include pores, edges, and/or walls adapted to form interconnected fluid channels. Liquids, gels, and other foams may also include or be cured to include apertures and fluid pathways. In some embodiments, the manifold layer 210 may additionally or alternatively comprise projections that form interconnected fluid pathways. For example, the manifold layer 210 may be molded to provide surface projections that define interconnected fluid pathways. Any or all of the surfaces of the manifold layer 210 may have an uneven, coarse, or jagged profile In some embodiments, the manifold layer 210 may comprise or be formed from a reticulated foam having pore sizes and free volume that may vary according to needs of a prescribed therapy. For example, a reticulated foam having a free volume of at least 90% may be suitable for many therapy applications, and a foam having an average pore size in a range of 400-600 microns (40-50 pores per inch) may be particularly suitable for some types of therapy. The tensile strength of the manifold layer 210 may also vary according to needs of a prescribed therapy. For example, the tensile strength of a foam may be increased for instillation of topical treatment solutions. The 25% compression load deflection of the manifold layer 210 may be at least 0.35 pounds per square inch, and the 65% compression load deflection may be at least 0.43 pounds per square inch. In some embodiments, the tensile strength of the manifold layer 210 may be at least 10 pounds per square inch. The manifold layer 210 may have a tear strength of at least 2.5 pounds per inch. In some embodiments, the manifold layer 210 may be a foam comprised of polyols such as polyester or polyether, isocyanate such as toluene diisocyanate, and polymerization modifiers such as amines and tin compounds. In one non-limiting example, the manifold layer 210 may be a reticulated polyurethane ether foam such as used in a V.A.C.® GRANUFOAM™ Dressing or a V.A.C.® VERAFLO™ Dressing, both available from KCI of San Antonio, Texas.

The thickness of the manifold layer 210 may also vary according to needs of a prescribed therapy. For example, the thickness of the manifold layer 210 may be decreased to relieve stress on other layers and to reduce tension on peripheral tissue. The thickness of the manifold layer 210 can also affect the conformability of the manifold layer 210. In some embodiments, a thickness in a range of about 4 millimeters to 10 millimeters may be suitable.

The fluid management layer 205 may comprise a means for controlling or managing fluid flow. In some embodiments, the fluid management layer 205 may comprise or be formed from a liquid-impermeable, elastomeric material. For example, the fluid management layer 205 may comprise or be formed from a polymer film. The fluid management layer 205 may also have a smooth or matte surface texture in some embodiments. A glossy or shiny finish better or equal to a grade B3 according to the SPI (Society of the Plastics Industry) standards may be particularly advantageous for some applications. In some embodiments, variations in surface height may be limited to acceptable tolerances. For example, the surface of the fluid management layer 205 may have a substantially flat surface, with height variations limited to 0.2 millimeters over a centimeter.

In some embodiments, the fluid management layer 205 may be hydrophobic. The hydrophobicity of the fluid management layer 205 may vary, but may have a contact angle with water of at least ninety degrees in some embodiments. In some embodiments, the fluid management layer 205 may have a contact angle with water of no more than 150 degrees. For example, in some embodiments, the contact angle of the fluid management layer 205 may be in a range of at least 90 degrees to about 120 degrees, or in a range of at least 120 degrees to 150 degrees. Water contact angles can be measured using any standard apparatus. Although manual goniometers can be used to visually approximate contact angles, contact angle measuring instruments can often include an integrated system involving a level stage, liquid dropper such as a syringe, camera, and software designed to calculate contact angles more accurately and precisely, among other things. Non-limiting examples of such integrated systems may include the FTÅ125, FTÅ200, FTÅ2000, and FTÅ4000 systems, all commercially available from First Ten Angstroms, Inc., of Portsmouth, VA, and the DTA25, DTA30, and DTA100 systems, all commercially available from Kruss GmbH of Hamburg, Germany. Unless otherwise specified, water contact angles herein are measured using deionized and distilled water on a level sample surface for a sessile drop added from a height of no more than 5 cm in air at 20-25° C. and relative humidity. Contact angles reported herein represent averages of 5-9 measured values, discarding both the highest and lowest measured values. The hydrophobicity of the fluid management layer 205 may be further enhanced with a hydrophobic coating of other materials, such as silicones and fluorocarbons, either as coated from a liquid, or plasma coated.

The fluid management layer 205 may also be suitable for welding to other layers, including the manifold layer 210. For example, the fluid management layer 205 may be adapted for welding to polyurethane foams using heat, radio frequency (RF) welding, or other methods to generate heat such as ultrasonic welding. RF welding may be particularly suitable for more polar materials, such as polyurethane, polyamides, polyesters and acrylates. Sacrificial polar interfaces may be used to facilitate RF welding of less polar film materials, such as polyethylene.

The area density of the fluid management layer 205 may vary according to a prescribed therapy or application. In some embodiments, an area density of less than 40 grams per square meter may be suitable, and an area density of about 20-30 grams per square meter may be particularly advantageous for some applications.

In some embodiments, for example, the fluid management layer 205 may comprise or be formed from a hydrophobic polymer, such as a polyethylene film. The simple and inert structure of polyethylene can provide a surface that interacts little, if any, with biological tissues and fluids, providing a surface that may encourage the free flow of liquids and low adherence, which can be particularly advantageous for many applications. More polar films suitable for laminating to a polyethylene film include polyamide, co-polyesters, ionomers, and acrylics. To aid in the bond between a polyethylene and polar film, tie layers may be used, such as ethylene vinyl acetate, or modified polyurethanes. An ethyl methyl acrylate (EMA) film may also have suitable hydrophobic and welding properties for some configurations.

As illustrated in the example of FIG. 2, the fluid management layer 205 may have one or more fluid restrictions 220, which can be distributed uniformly or randomly across the fluid management layer 205. The fluid restrictions 220 may be bi-directional and pressure-responsive. For example, the fluid restrictions 220 can generally comprise an elastic passage that is normally unstrained to substantially reduce liquid flow, and can expand in response to a pressure gradient or deformation of the fluid management layer 205. In some embodiments, the fluid restrictions 220 may comprise perforations in the fluid management layer 205. Perforations may be formed by removing material from the fluid management layer 205. For example, perforations may be formed by cutting through the fluid management layer 205, which may also deform the edges of the perforations in some embodiments. In the absence of a pressure gradient across the perforations or deformation of the fluid management layer 205, the passages may be sufficiently small to form a seal or flow restriction, which can substantially reduce or prevent liquid flow. Additionally or alternatively, one or more of the fluid restrictions 220 may be an elastomeric valve that is normally closed when unstrained to substantially prevent liquid flow, and can open in response to a pressure gradient or deformation of the fluid management layer 205. A fenestration in the fluid management layer 205 may be a suitable valve for some applications. Fenestrations may also be formed by removing material from the fluid management layer 205, but the amount of material removed and the resulting dimensions of the fenestrations may be an order of magnitude less than perforations, and may not deform the edges.

Figure 3:
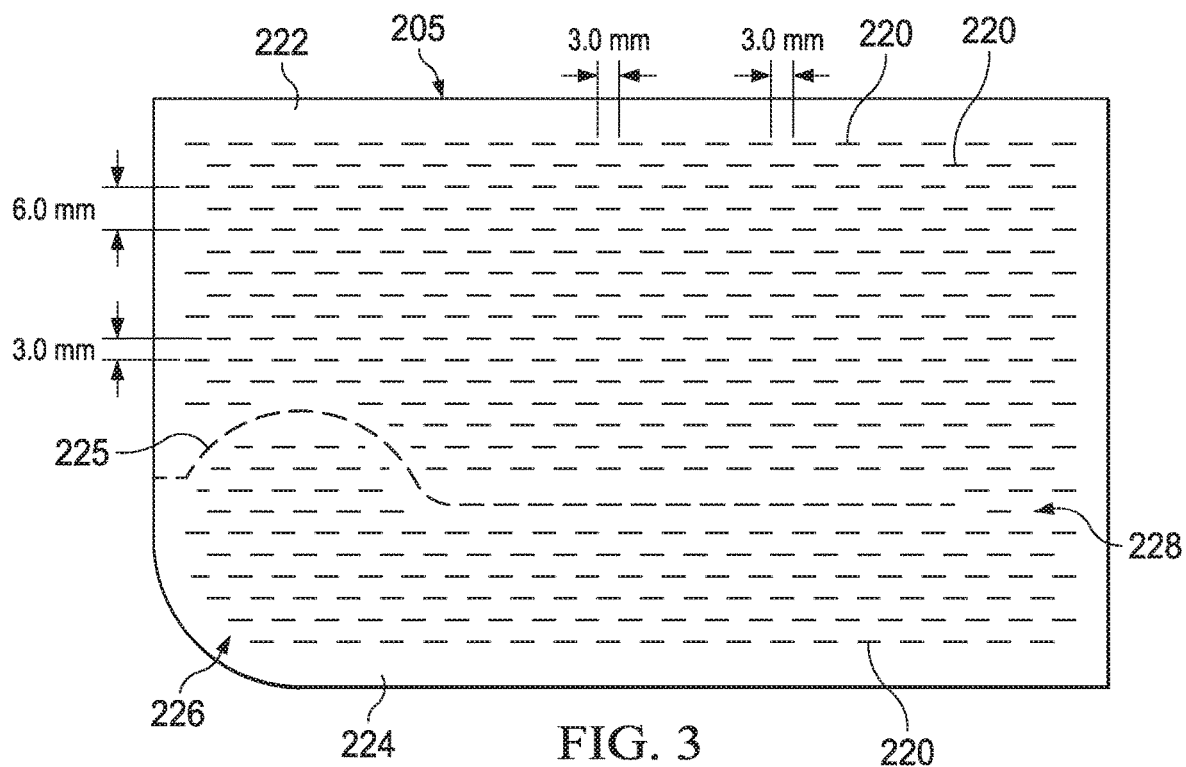
FIG. 3 is a detailed view of an example configuration of fluid restrictions in a layer that may be associated with some embodiments of the tissue interface of FIG. 2.

FIG. 3 is a schematic view of an example of the fluid management layer 205, illustrating additional details that may be associated with some embodiments. For example, some embodiments of the fluid restrictions 220 may comprise one or more slots or combinations of slots in the fluid management layer 205. In some examples, the fluid restrictions 220 may comprise linear slots having a length less than 4 millimeters and a width less than 1 millimeter. The length may be at least 2 millimeters, and the width may be at least 0.4 millimeters in some embodiments. A length of about 3 millimeters and a width of about 0.8 millimeter may be particularly suitable for many applications. As illustrated in the example of FIG. 3, the fluid restrictions 220 may each consist essentially of one or more linear slots having a length of about 3 millimeters. A tolerance of about 0.1 millimeter may also be acceptable. Such dimensions and tolerances may be achieved with a laser cutter, for example. Slots of such configurations may function as imperfect valves that substantially reduce liquid flow in a normally closed or resting state. For example, such slots may form a flow restriction without being completely closed or sealed. The slots can expand or open wider in response to a pressure gradient or deformation of the fluid management layer 205 to allow increased liquid flow.

FIG. 3 additionally illustrates an example of a uniform distribution pattern of the fluid restrictions 220. In FIG. 3, the fluid restrictions 220 configured to be substantially coextensive with the fluid management layer 205, and are distributed across the fluid management layer 205 in a grid of parallel rows and columns, in which the slots are also mutually parallel to each other. In some embodiments, the rows may be spaced about 3 millimeters on center, and the fluid restrictions 220 within each of the rows may be spaced about 3 millimeters on center as illustrated in the example of FIG. 3. The fluid restrictions 220 in adjacent rows may be aligned or offset. For example, adjacent rows may be offset, as illustrated in FIG. 3, so that the fluid restrictions 220 are aligned in alternating rows and separated by about 6 millimeters. The spacing of the fluid restrictions 220 may vary in some embodiments to increase the density of the fluid restrictions 220 according to therapeutic requirements.

One or more of the components of the dressing 110 may additionally be treated with an antimicrobial agent in some embodiments. For example, the manifold layer 210 may be a foam, mesh, or non-woven coated with an antimicrobial agent. In some embodiments, one or more components may be treated with antimicrobial elements, such as fibers coated with an antimicrobial agent. Additionally or alternatively, in some embodiments, one or more components may be may be a polymer coated or mixed with an antimicrobial agent. In other examples, other components such as the fluid conductor may additionally or alternatively be treated with one or more antimicrobial agents. Suitable antimicrobial agents may include, for example, metallic silver, PHMB, iodine or its complexes and mixes such as povidone iodine, copper metal compounds, chlorhexidine, or some combination of these materials.

Two or more components of the dressing 110, for example, the fluid management layer 205 and the manifold layer 210, may be bonded or otherwise secured to one another with a solvent or non-solvent adhesive, or with thermal welding.

In some embodiments, the tissue interface 120 may be configured to provide for attachment for a fluid conductor at a location spaced away from the tissue site receiving negative pressure therapy. For example, the tissue interface 120 may include both a tissue portion generally configured to be placed within, over, or otherwise proximate to the tissue site and a bridge portion configured to be extended away from the tissue portion, for example, to provide a location apart from the tissue site at which a connection to the negative-pressure source 105 can be made. In various embodiments, one or more of the layers that make up the tissue interface 120 may include both the tissue portion and the bridge portion.

For example, referring again to the embodiment of FIG. 2, the manifold layer 210 may comprise both a tissue portion 212 and a bridge portion 214. The bridge portion 214 may be coupled to the tissue portion 212. Also, the bridge portion 214 may comprise a distal end 216 configured to be extended away from the tissue portion 212 while the bridge portion 214 remains coupled to the tissue portion 212.

For example, in some embodiments, the manifold layer 210 may comprise one or more lines of detachment 219 generally separating the tissue portion 212 and the bridge portion 214. In the embodiment of FIG. 2, the one or more lines of detachment 219 of the manifold layer 210 may include or may be perforations 215. Additionally or alternatively, in some embodiments, lines of detachment 219 in the manifold layer 210 may include slits or other suitable lines of weakness along which the manifold layer 210 can be separated. Additionally or alternatively, in some embodiments, lines of detachment 219 in the manifold layer 210 may include a cut or void-space at least partially separating the tissue portion 212 from the bridge portion 214. In various embodiments, any suitable number of lines of detachment 219 may be used to form a desired configuration of the manifold layer 210. For example, in the embodiment of FIG. 2, a single line of the perforations 215 in the manifold layer 210 define the tissue portion 212 and the bridge portion 214, although in some embodiments, multiple lines of detachment 219 may be present in the manifold layer 210.

Also in the embodiment of FIG. 2, the fluid management layer 205 may likewise include both a tissue portion 222 and a bridge portion 224 having a distal end 226 and separated from the tissue portion 222 by one or more lines of detachment, such as perforations 225. In some embodiments, the fluid management layer 205 may be coupled to the manifold layer 210 such that the tissue portion 212, the bridge portion 214, and the perforations 215 in the manifold layer 210 are substantially aligned with, or generally coextensive with, the tissue portion 222, the bridge portion 224, and the perforations 225 in the fluid management layer 205. Additionally or alternatively, in some embodiments, the fluid management layer 205 may cover only a portion of the first surface or second surface of the manifold layer 210. For example, in some embodiments, the fluid management layer 205 may include only the tissue portion 222. In some embodiments, the bridge portion 224 of the fluid management layer 205 may be removable to more-fully expose the bridge portion 214 of the manifold layer 210. For example, the bridge portion 224 of the fluid management layer 205 may be relatively weakly-coupled to the bridge portion 214 of the manifold layer 210 to enable the removal of the bridge portion 224.

Also, in some embodiments, the lines of detachment may vary between the manifold layer 210 and the fluid management layer 205. For example, in some embodiments, the lines of detachment in the manifold layer 210 may include cuts or void-spaces while the lines of detachment in the fluid management layer 205 include perforations or slits.

In various embodiments, the bridge portion 214 of the manifold layer 210 may take any suitable shape or form in which the distal end 216 of the bridge portion 214 can be extended away from the tissue portion 212. Likewise, the bridge portion 224 of the fluid management layer 205 may take any suitable shape of form in which the distal end 226 of the bridge portion 224 can be extended away from the tissue portion 222.

In the embodiment of FIG. 2, the bridge portions 214, 224 are illustrated in a first position in which the bridge portions 214, 224 are not extended away from the tissue portions 212, 222. In the first position illustrated in FIG. 2, the bridge portions 214, 224 may be disposed adjacent to edges 217, 227 of the respective tissue portions 212, 222.

In various embodiments, the bridge portions 214, 224 may be configured to be extended away from the tissue portions 212, 222 by rotation of the bridge portions 214, 224 about one or more axes with respect to the respective tissue portions 212, 222. For example, the bridge portions 214, 224 may be configured to be rotated with respect to the respective tissue portions 212, 222 in a direction substantially parallel to the first surface and the second surface of the manifold layer 210 and/or the respective surfaces of the fluid management layer 205. Additionally or alternatively, the bridge portions 214, 224 may be configured to be rotated with respect to the tissue portions 212, 222 in a direction substantially perpendicular to the first surface and the second surface.

Figure 4:
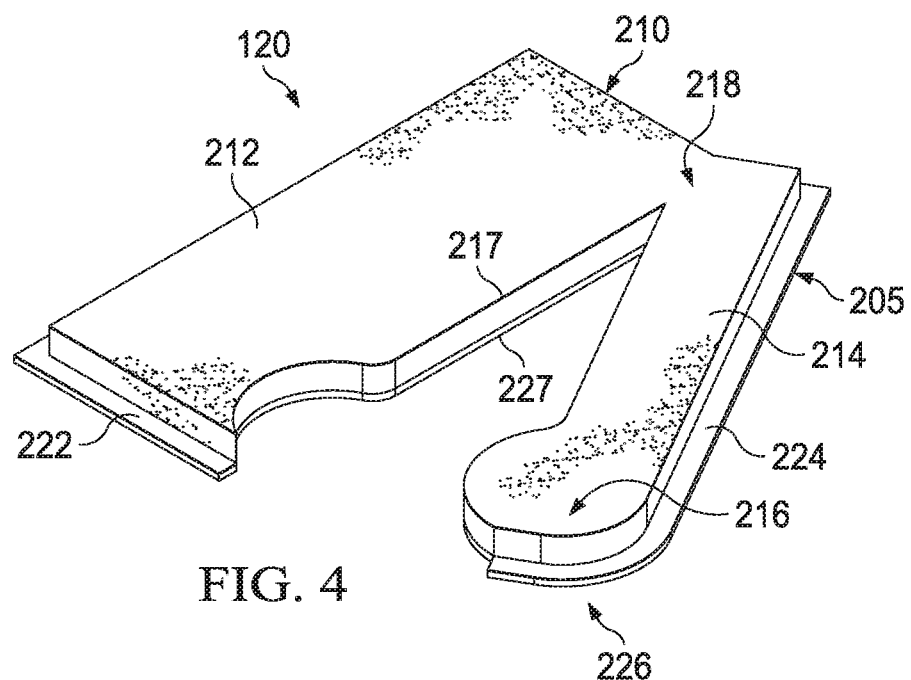
FIG. 4 is a perspective view the tissue interface of FIG. 2 in an extended position.

For example, FIG. 4 is a perspective view of the tissue interface 120 of FIG. 2 in another position. In the embodiment of FIG. 4, the bridge portions 214, 224 are illustrated having been rotated to a second position in which the distal ends 216, 226 of the respective bridge portions 214, 224 may be further away from the respective tissue portions 212, 222 than in the first position. The bridge portions 214, 224 may be rotated in a direction substantially parallel to the first surface and/or the second surface of the manifold layer 210 and/or the respective surfaces of the fluid management layer 205. For example, the bridge portions 214, 224 may be configured to be rotated about an axis substantially perpendicular to the first surface and/or the second surface of the manifold layer 210 and/or the respective surfaces of the fluid management layer 205. In some embodiments, such as illustrated in FIGS. 2 and 4, the manifold layer 210 may include a pivot zone 218 and/or the fluid management layer 205 may include a pivot zone 228 generally configured to allow the bridge portions 214, 224 to be rotated in a direction substantially parallel to the first surface and/or the second surface of the manifold layer 210 and/or the respective surfaces of the fluid management layer 205, for example, without substantial bunching or tearing. For example, the pivot zones 218, 228 may include one or more holes, slots, perforations, or combinations thereof, enabling the bridge portions 214, 224 to be rotated to the second position.

Figure 5:
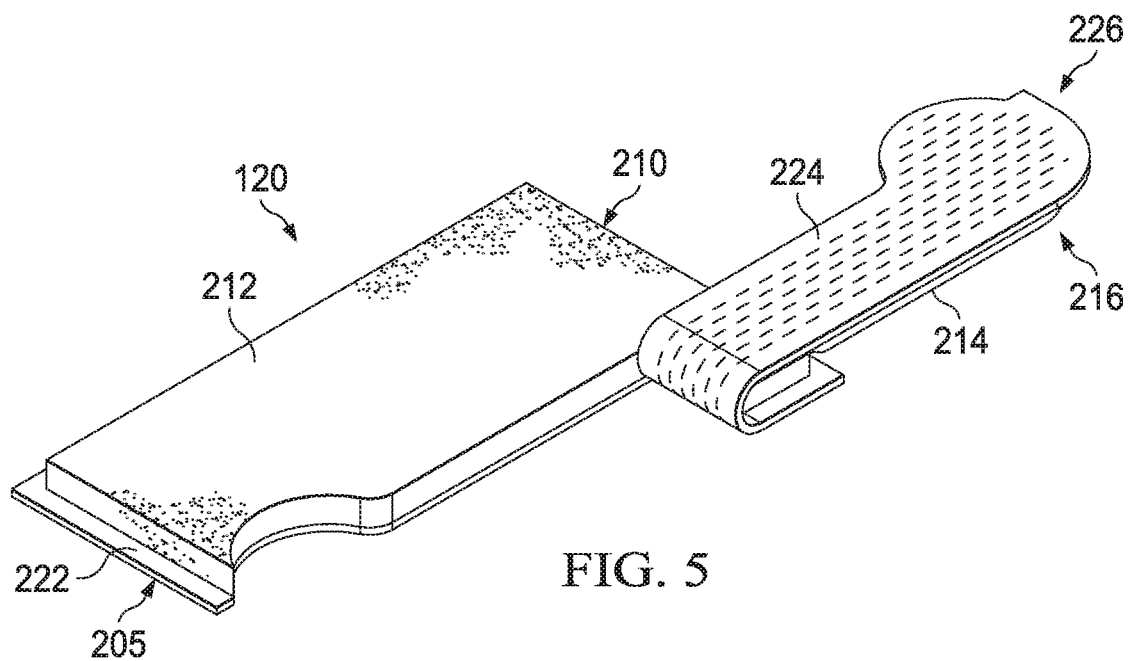
FIG. 5 is a perspective view of the tissue interface of FIG. 2 in another extended position.

Additionally or alternatively, FIG. 5 is a perspective view of the tissue interface 120 of FIG. 2 in another position. In the embodiment of FIG. 5, the bridge portions 214, 224 are illustrated having been rotated to a second position in which the distal ends 216, 226 of the bridge portions 214, 224 may be further away from the respective tissue portions 212, 222 than in the first position. In the second position illustrated in FIG. 5, the bridge portions 214, 224 may be rotated in a direction substantially perpendicular to the first surface and the second surface of the manifold layer 210 and/or the respective surfaces of the fluid management layer 205. For example, the bridge portions 214, 224 may be configured to be rotated about an axis substantially parallel to the first surface and/or the second surface of the manifold layer 210 and/or the respective surfaces of the fluid management layer 205. For example, the bridge portions 214, 224 may be configured to be folded, for example, about 180 degrees, such that the distal ends 216, 226 of the bridge portions 214, 224 are disposed further away from the respective tissue portions 212, 222.

Figure 6:
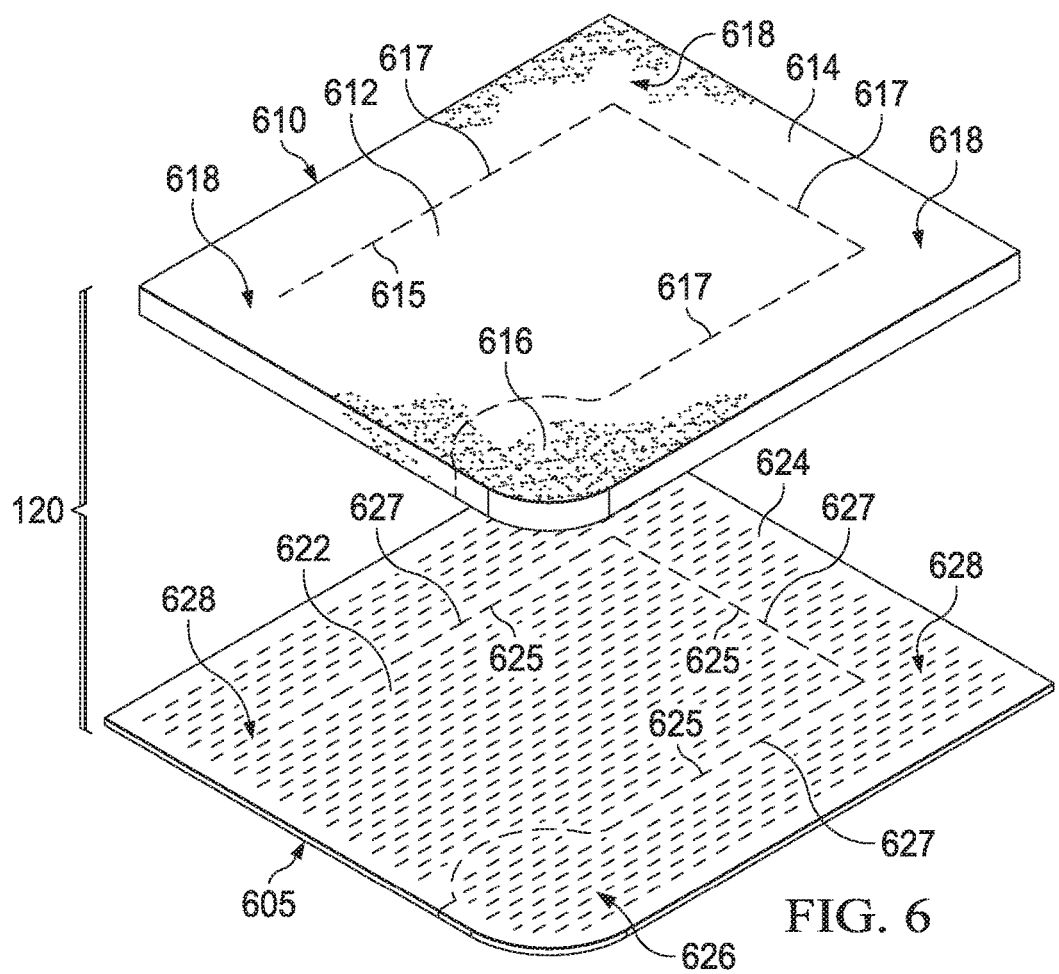
FIG. 6 is an exploded view of another example of a tissue interface, illustrating additional details that may be associated with some example embodiments of the therapy system and the dressing of FIG. 1.

Additionally or alternatively, FIG. 6 is an exploded view of another example of the tissue interface 120 likewise including a manifold layer 610 and a fluid management layer 605. In the embodiment of FIG. 6, the bridge portions 614, 624 are illustrated in a first position in which the bridge portions 614, 624 are not extended away from the respective tissue portions 612, 622. In the first position illustrated in FIG. 6, the bridge portions 614, 624 may at least partially circumscribe the respective tissue portions 612, 622. For example, in the first position illustrated in FIG. 6, respective portions the bridge portion 614 of the manifold layer 610 may be disposed adjacent to two or more edges 617 of the tissue portion 612 of the manifold layer 610 and, likewise, respective portions the bridge portion 624 of the fluid management layer 605 may be disposed adjacent to two or more edges 627 of the tissue portion 622 of the fluid management layer 605. The bridge portions 614, 624 may be separated from the respective tissue portions 612, 622 by perforations 615 the manifold layer 610 and perforations 625 in the fluid management layer 605, respectively.

Figure 7:
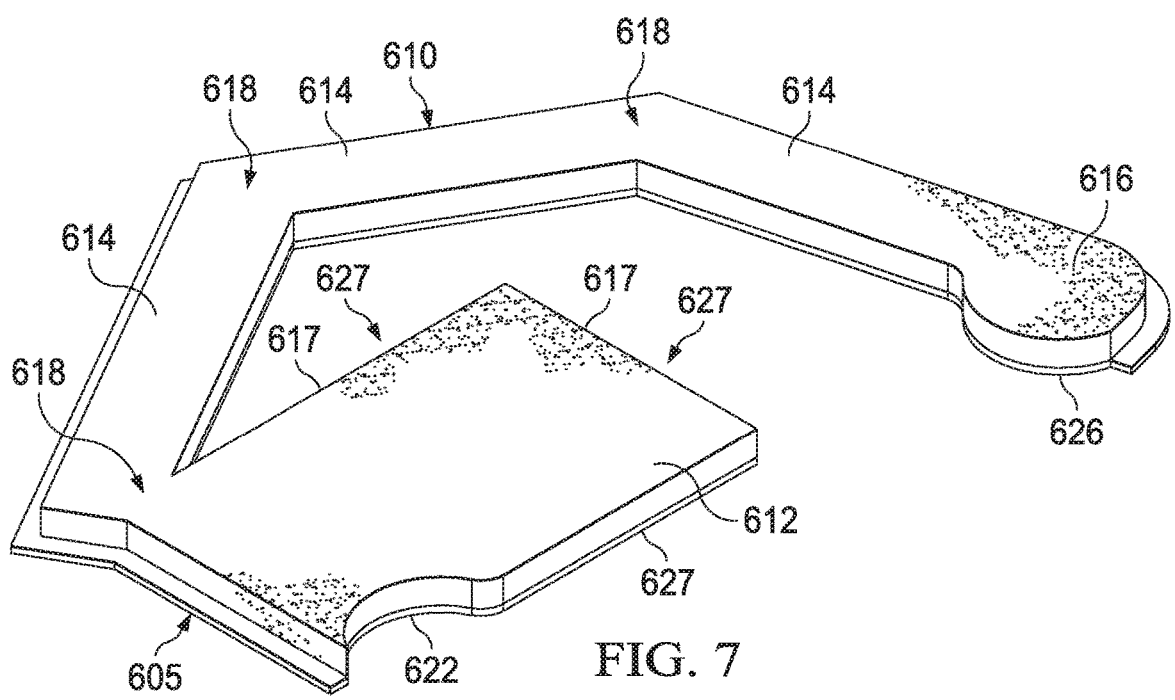
FIG. 7 is a perspective view of the tissue interface of FIG. 6 in an extended position.

FIG. 7 is a perspective view of the tissue interface 120 of FIG. 6 in another position. In the embodiment of FIG. 7, the bridge portions 614, 624 are illustrated having been rotated to a second position in which the distal ends 616, 626 of the respective bridge portions 614, 624 may be further away from the respective tissue portions 612, 622 than in the first position. The bridge portions 614, 624 may be rotated in one or more directions substantially parallel to the first surface and/or the second surface of the manifold layer 610 and/or the respective surfaces of the fluid management layer 605. For example, the bridge portions 614, 624 may be configured to be rotated about one or more axes substantially perpendicular to the first surface and/or the second surface of the manifold layer 610 and/or the respective surfaces of the fluid management layer 605. In the embodiment of FIGS. 6 and 7, the manifold layer 610 may include multiple pivot zones 618 and/or the fluid management layer 605 may include multiple pivot zones 628 generally configured to allow the bridge portions 614, 624 or portions thereof to be rotated in one or more directions substantially parallel to the first surface and/or the second surface of the manifold layer 210 and/or the respective surfaces of the fluid management layer 605.

Figure 8:
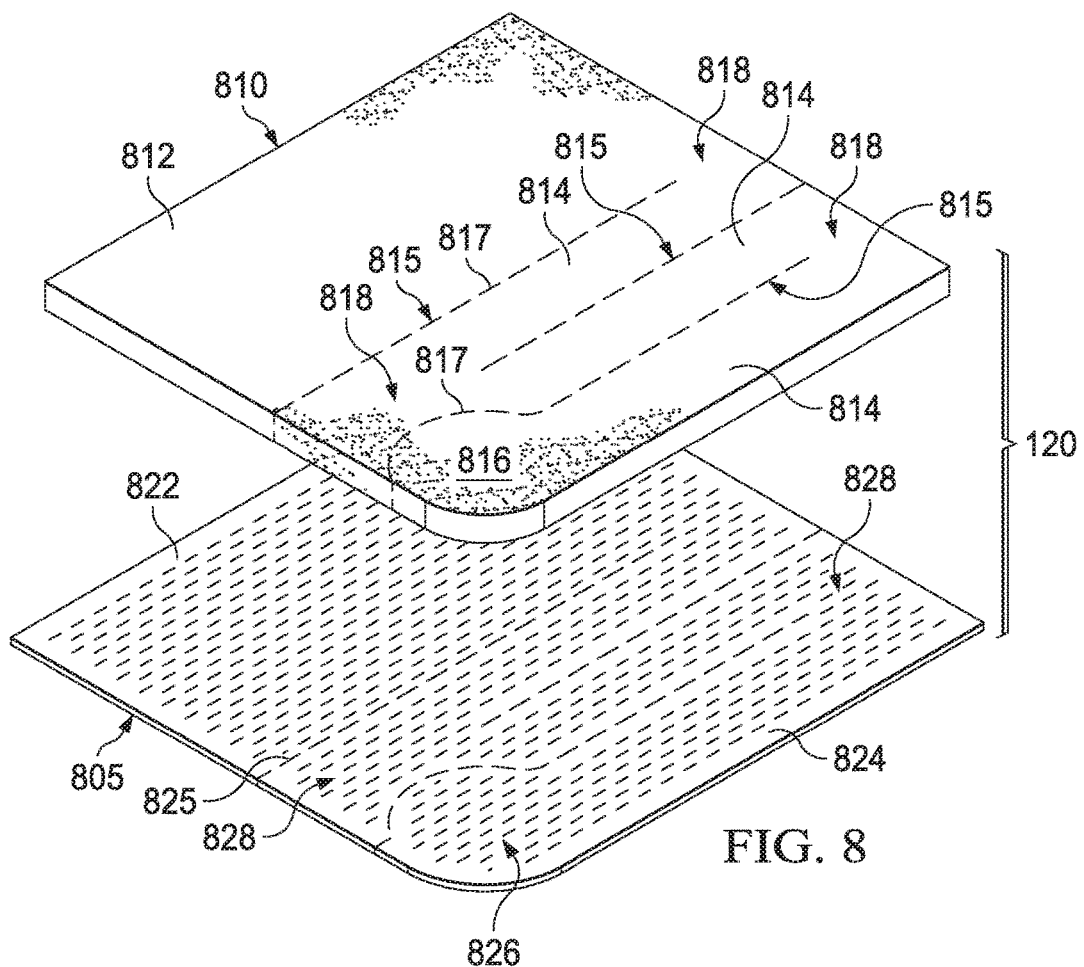
FIG. 8 is an exploded view of another example of a tissue interface, illustrating additional details that may be associated with some example embodiments of the therapy system and the dressing of FIG. 1.

Additionally or alternatively, FIG. 8 is an exploded view of another example of the tissue interface 120 likewise including a manifold layer 810 and a fluid management layer 805. In the embodiment of FIG. 8, the bridge portions 814, 824 are illustrated in a first position in which the bridge portions 814, 824 are not extended away from the respective tissue portions 812, 824. In the first position of the embodiment illustrated in FIG. 8, the bridge portion 814 of the manifold layer 810 may be disposed adjacent to an edge 817 of the tissue portion 812 and, likewise, the bridge portion 824 of the fluid management layer 805 may be disposed adjacent to an edge 827 of the tissue portion 822. The bridge portions 814, 824 may be separated from the respective tissue portions 812, 822 by perforations 815 in the manifold layer 810 and perforations 825 in the fluid management layer 805, respectively. In the embodiment of FIG. 8, the bridge portions 814, 824 comprise a serpentine pattern formed by additional perforations 815, 825 disposed within the bridge portions 814, 824.

Figure 9:
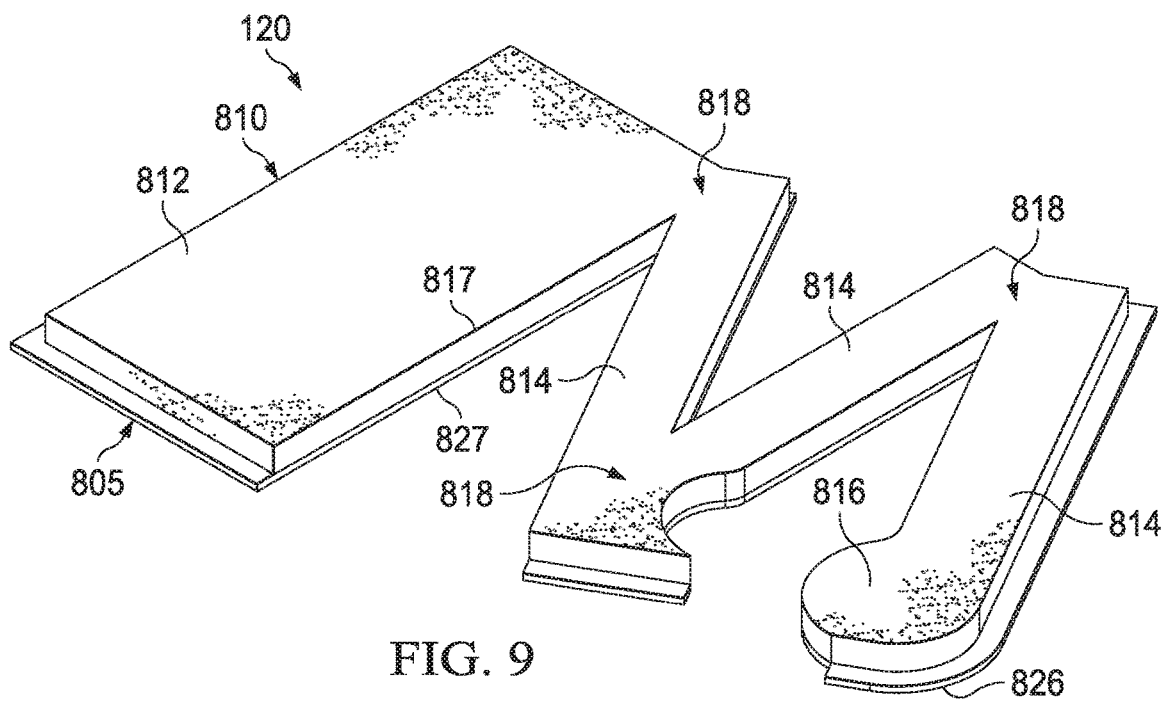
FIG. 9 is a perspective view of the tissue interface of FIG. 8 in an extended position.

FIG. 9 is a perspective view of the tissue interface 120 of FIG. 8 in another position. In the embodiment of FIG. 9, the bridge portions 814, 824 are illustrated having been rotated to a second position in which the distal ends 816, 826 of the respective bridge portions 814, 824 may be further away from the respective tissue portions 812, 822 than in the first position. The bridge portions 814, 824 may be rotated in one or more directions substantially parallel to the first surface and/or the second surface of the manifold layer 810 and/or the respective surfaces of the fluid management layer 805. For example, the bridge portions 814, 824 may be configured to be rotated about one or more axes substantially perpendicular to the first surface and/or the second surface of the manifold layer 810 and/or the respective surfaces of the fluid management layer 805. In the embodiment of FIGS. 8 and 9, the manifold layer 810 may include multiple pivot zones 818 and/or the fluid management layer 805 may include multiple pivot zones 828 generally configured to allow the bridge portions 814, 824 or portions thereof to be rotated in one or more directions substantially parallel to the first surface and/or the second surface of the manifold layer 210 and/or the respective surfaces of the fluid management layer 805.

Figure 10:
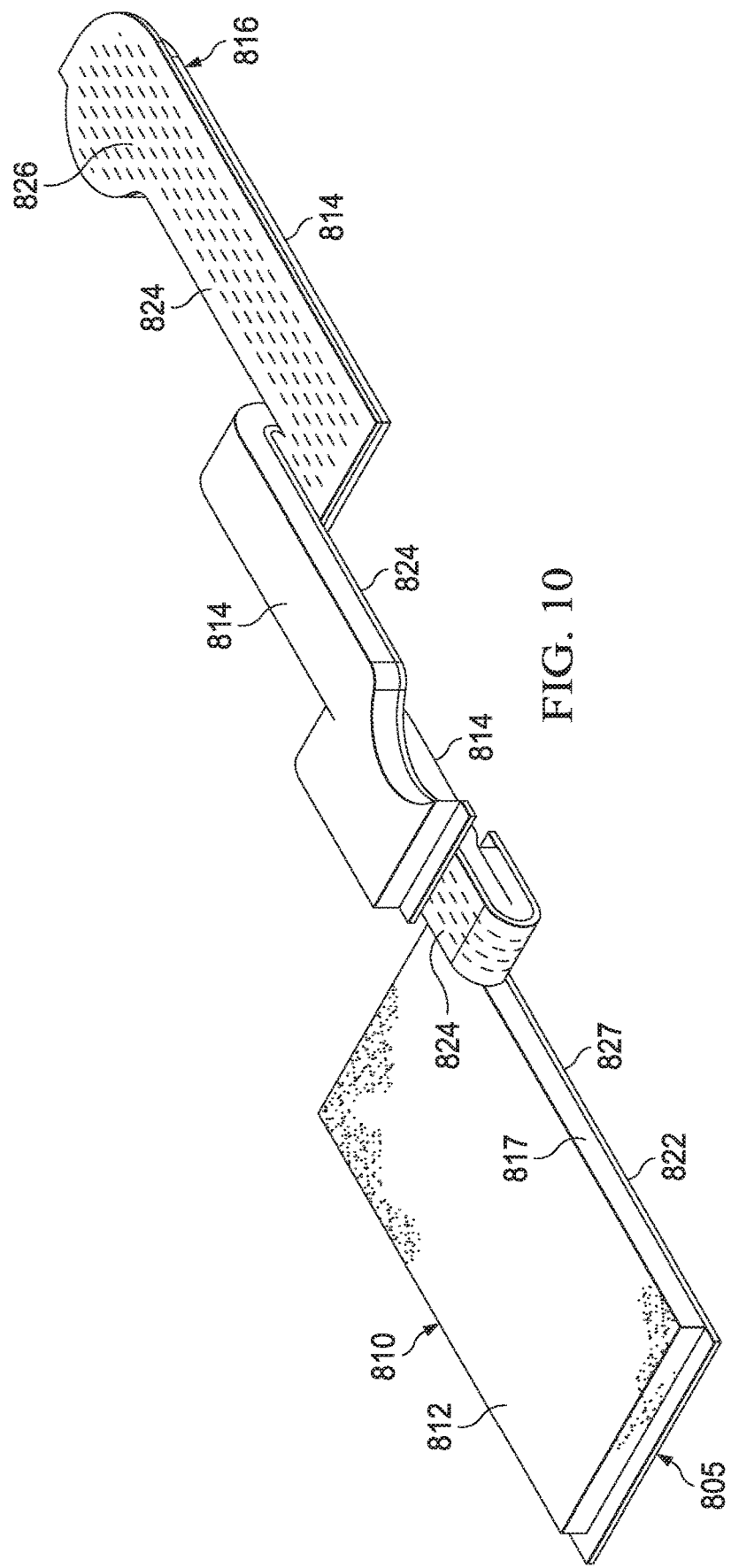
FIG. 10 is a perspective view of the tissue interface of FIG. 8 in another extended position.

Additionally or alternatively, FIG. 10 is a perspective view of the tissue interface 120 of FIG. 8 in another position. In the embodiment of FIG. 10, the bridge portions 814, 824 are illustrated having been rotated to a second position in which the distal ends 816, 826 of the bridge portions 814, 824 may be further away from the respective tissue portions 812, 822 than in the first position. In the second position illustrated in FIG. 10, the bridge portions 814, 824 may be rotated in one or more directions substantially perpendicular to the first surface and the second surface of the manifold layer 810 and/or the respective surfaces of the fluid management layer 805. For example, the bridge portions 814, 824 may be configured to be rotated about one or more axes substantially parallel to the first surface and/or the second surface of the manifold layer 810 and/or the respective surfaces of the fluid management layer 805. For example, the bridge portions 814, 824 may be configured to be folded, for example, about 180 degrees, such that the distal ends 816, 826 of the bridge portions 814, 824 are disposed further away from the respective tissue portions 812, 822.

Figure 11:
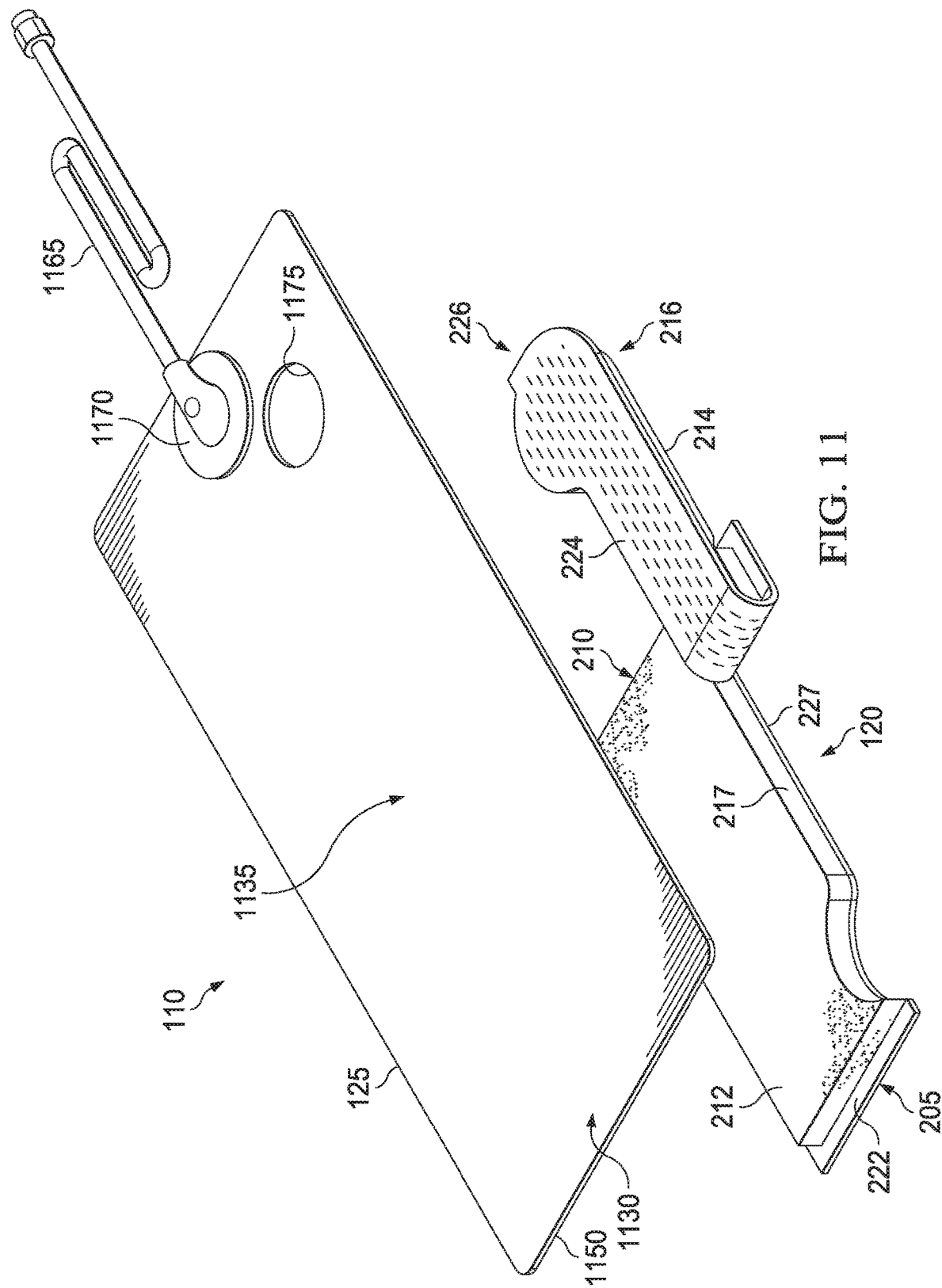
FIG. 11 is a partially-exploded view of an example of a dressing including the example tissue interface of FIG. 2 in an extended position.

FIG. 11 is an exploded view of an embodiment of the dressing 110, including the embodiment of the tissue interface 120 disposed in a second, extended position, for example, as discussed with respect to FIG. 4. In the embodiment of FIG. 11 the dressing 110 illustrates the cover 125 positioned with respect to the tissue interface 120.

In some embodiments, the cover 125 may be sized to extend over the entirety of the tissue interface 120 and enclose the tissue interface 120 at a tissue site. The cover 125 may have a periphery 1130 surrounding or around an interior portion 1135. The interior portion 1135 may correspond to a surface area of the tissue interface 120 (for example, the manifold layer 210 and fluid management layer 205). For example, the cover 125 may be sized such that the interior portion 1135 is sufficient to cover the tissue interface 120 in a second position in which the distal end 216 is extended away from the tissue portion 212. Alternatively, in some embodiments, two or more of the covers 125 each extending over a portion of the tissue interface 120 may be used together to cover the tissue interface 120 and enclose the tissue interface 120 at a tissue site.

In the example of FIG. 11, the dressing 110 may further include an attachment device, such as an adhesive 1150. The adhesive 1150 may be a layer and may be applied to a surface of the cover 125, for example, the periphery 1130 of the cover 125, a portion of the cover 125, or the entire cover 125. In some embodiments, the adhesive 1150 may be continuous or discontinuous. Discontinuities in the adhesive 1150 may be provided by apertures or holes (not shown) in the adhesive 1150. The apertures or holes in the adhesive 1150 may be formed after application of the adhesive 1150 or by coating the adhesive 1150 in patterns on a carrier layer, such as, for example, a side of the cover 125. Apertures or holes in the adhesive 1150 may also be sized to enhance the MVTR of the dressing 110 in some example embodiments.

FIG. 11 also illustrates an example of a fluid conductor 1165 and a dressing interface 1170. As shown in the example of FIG. 11, the fluid conductor 1165 may be a flexible tube, which can be fluidly coupled on one end to the dressing interface 1170. The dressing interface 1170 may be an elbow connector, as shown in the example of FIG. 11, which can be placed over an aperture 1175 in the cover 125 to provide a fluid path between the fluid conductor 1165 and the tissue interface 120 when the cover 125 is positioned with respect to the tissue interface 120. In some embodiments, for example, as illustrated in FIG. 11, the aperture 1175 may be disposed in the cover 125 near the periphery 1130 of the cover 125. For example, disposition of the aperture 1175 at a position within or relatively near the periphery 1130 may enable the aperture to be disposed over the distal ends 216, 226 of the bridge portions 214, 224 of the layer of the tissue interface 120 when the tissue interface 120 is positioned in a second, extended position.

Figure 12:
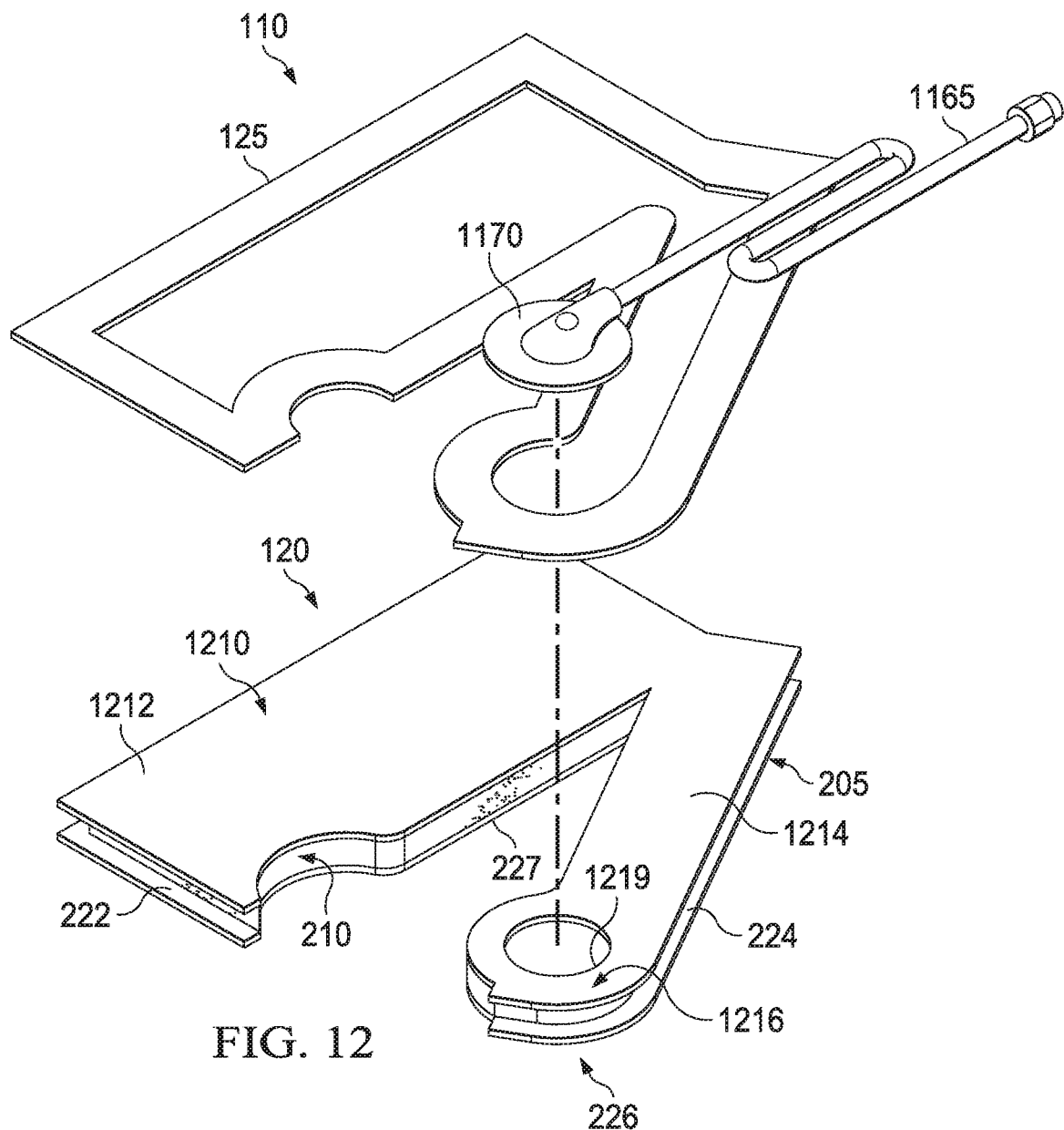
FIG. 12 is a partially-exploded view of an example of a dressing including another example of a tissue interface in an extended position.

FIG. 12 is an exploded view of an embodiment of the dressing 110, including another embodiment of the tissue interface 120 disposed in a second, extended position. Referring to FIG. 12, in some embodiments, the tissue interface 120 may further comprise a barrier layer 1210 coupled to the manifold layer 210 opposite the fluid management layer 205. In some embodiments, the barrier layer 1210 may be a sealing layer comprising or formed from a soft, pliable material suitable for providing a fluid seal over at least a portion of the manifold layer 210. In some embodiments, the barrier layer 1210 may comprise one or more of the materials previously disclosed with respect to the fluid management layer 205. For example, the barrier layer 1210 may comprise a film of a polyethylene, a polyamide, a co-polyester, an ionomer, or an acrylic. As also disclosed with respect to the fluid management layer 205, the barrier layer 1210 may also be suitable for welding to other layers, including the manifold layer 210.

Additionally, as shown in FIG. 12, the barrier layer 1210 may also include both a tissue portion 1212 and a bridge portion 1214 having a distal end 1216. In some embodiments, the distal end 1216 of the bridge portion 1214 of the barrier layer 1210 may include a fluid aperture 1219 generally configured to provide a route of unrestricted fluid communication through the barrier layer 1210. Additionally or alternatively, in some embodiments, the bridge portion 1214 of the barrier layer 1210 may be removable to more-fully expose the bridge portion 1214 of the manifold layer 210. For example, the bridge portion 1214 of the barrier layer 1210 may be relatively weakly-coupled to the bridge portion 214 of the manifold layer 210 to enable the removal of the bridge portion 224. In some embodiments, the barrier layer 1210 may allow for use of a cover 125 generally configured to seal the edges of the barrier layer 1210 to a tissue site. For example, as shown in FIG. 12, the cover 125 may comprise a strip of material generally configured to extend around a perimeter of the tissue interface 120 to seal the tissue interface 120 to a tissue site. The strip of material may be continuous or discontinuous. For example, in some embodiments, the cover 120 may include multiple strips of material configured to seal the tissue interface 120 to a tissue site. As similarly disclosed with respect to FIG. 11, FIG. 12 also illustrates an embodiment including the fluid conductor 1165 and the dressing interface 1170 placed with respect to the tissue interface 120.

Also, in some embodiments, the barrier layer 1210 may be configured to extend beyond the edges of the manifold layer 210. Any portions of the barrier layer 1210 extending beyond the manifold layer 210 may be folded around the manifold layer 210 such that the manifold layer 210 does not have any exposed edges. Not intending to be bound by theory, configuring the barrier layer 1210 to cover the edges of the manifold layer 210, such that the edges of the manifold layer 210 are not exposed, may reduce the potential for irritation of the tissue site or peripheral tissue resulting from exposure to the manifold layer 210. Additionally or alternatively, in some embodiments, the fluid management layer 205 (or, in some embodiments, fluid management layer 605 or fluid management layer 805) may similarly be configured to extend beyond the edges of the manifold layer 210 (or, in respective embodiments, manifold layer 610 or manifold layer 810) such that the manifold layer 210 does not have exposed edges.

Figure 13:
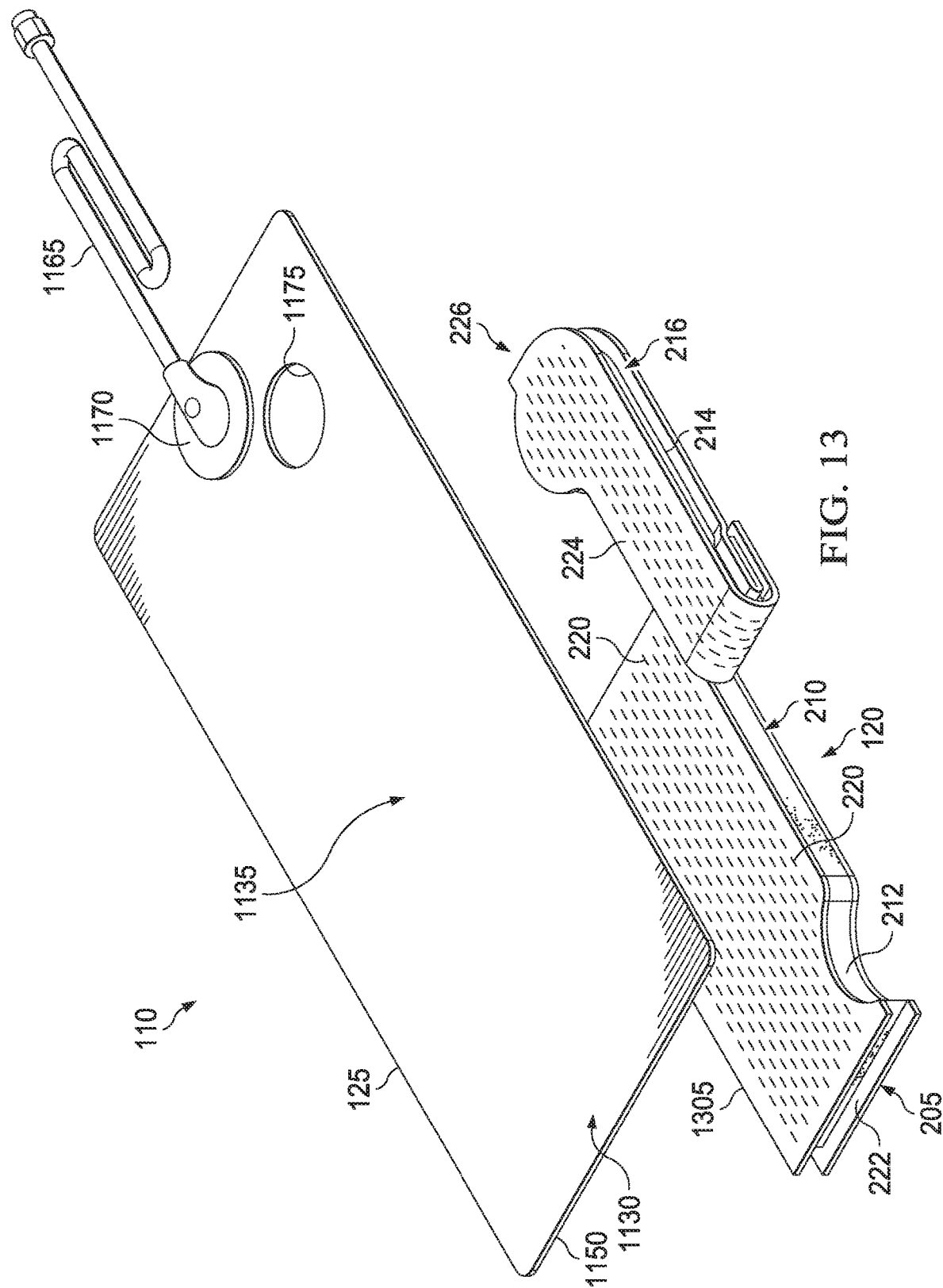
FIG. 13 is a partially-exploded view of an example of a dressing including another example of a tissue interface in an extended position.

FIG. 13 is an exploded view of an embodiment of the dressing 110, including another embodiment of the tissue interface 120 disposed in a second, extended position. Referring to FIG. 13, in some embodiments, in some embodiments, the tissue interface 120 may further comprise a second fluid management layer 1305 coupled to the manifold layer 210 opposite the fluid management layer 205. As similarly disclosed with respect to the fluid management layer 205, second fluid management layer 1305 may include one or more fluid restrictions 220, which can be distributed uniformly or randomly across the second fluid management layer 1305. Embodiments of the tissue interface 120 including both the fluid management layer 205 and the second fluid management layer 1305 disposed on the surfaces of the manifold layer 210 may provide additional placement options for the tissue interface 120 with respect to a tissue site. For example, in such embodiments, the tissue interface 120 may be disposed with either side facing the tissue site because negative pressure can be distributed across both surfaces of the tissue interface 120.

Figure 14:
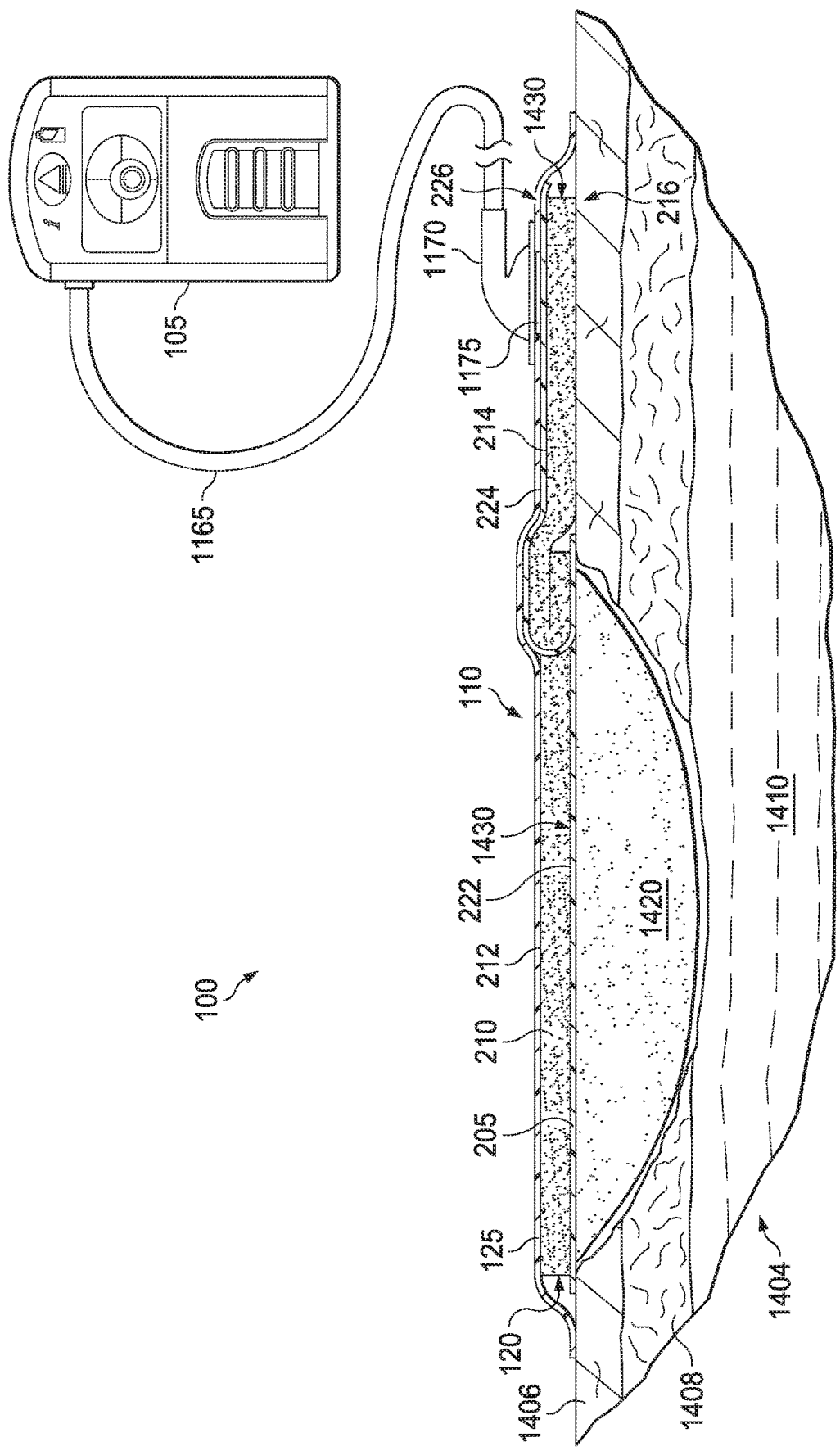
FIG. 14 is a partial cross-sectional view of the therapy system of FIG. 1 positioned with respect to a tissue site.

FIG. 14 depicts an example of the therapy system 100 implemented in the treatment of a tissue site 1404 of a patient. The tissue site 1404 may extend through or otherwise involve an epidermis 1406, a dermis 1408, and a subcutaneous tissue 1410. In some embodiments, the tissue site 1404 may include a sub-surface portion that extends below the surface of the epidermis 1406. Additionally or alternatively, in some embodiments, the tissue site 1404 may include a surface portion that predominantly resides on the surface of the epidermis 1406, such as, for example, an incision. The therapy system 100 may provide therapy to, for example, the epidermis 1406, the dermis 1408, and the subcutaneous tissue 1410, regardless of the positioning of the therapy system 100 or the type of tissue site. In some embodiments, the tissue site 1404 may be disposed in a location in which it is difficult to provide fluid connection to the negative-pressure source 105. For example, the tissue site 1404 might be part of a patient's foot, such as the patient's heel, or another difficult location, such as an elbow. The therapy system 100 may also be utilized, without limitation, at other tissue sites. The geometry and dimensions of the tissue interface 120, the cover 125, or both may vary to suit a particular application or anatomy. For example, the geometry or dimensions of the tissue interface 120 and the cover 125 may be adapted to provide an effective and reliable seal against challenging anatomical surfaces, such as an elbow or heel, at and around a tissue site.

In some embodiments, for example, in the embodiment of FIG. 14, the therapy system 100 may include an optional tissue interface component, such as an interface manifold 1420. The interface manifold 1420 is an optional component that may be omitted for different types of tissue sites or different types of therapy using reduced pressure, such as, for example, epithelialization, tissue closure, incision treatment, and others. If present, the interface manifold 1420 may be adapted to be positioned proximate to or adjacent to the tissue site 1404, such as, for example, by cutting or otherwise shaping the interface manifold 1420 in any suitable manner to fit the tissue site 1404. The interface manifold 1420 may be adapted to be positioned in fluid communication with the tissue site 1404 to distribute reduced pressure to the tissue site 1404. In some embodiments, the interface manifold 1420 may be positioned in direct contact with the tissue site 1404. The interface manifold 1420 may be formed from any manifold material or flexible bolster material that provides a vacuum space, or treatment space, such as, for example, a porous and permeable foam or foam-like material, a member formed with pathways, a graft, or a gauze. As a more specific, non-limiting example, the interface manifold 1420 may be a reticulated, open-cell polyurethane or polyether foam that allows good permeability of fluids while under a reduced pressure. One such foam material is used in the V.A.C.® GRANUFOAM™ Dressing available from Kinetic Concepts, Inc. (KCI) of San Antonio, Texas. A material with a higher or lower density than the material of the V.A.C.® GRANUFOAM™ Dressing may be desirable for the interface manifold 1420 depending on the application. Among the many possible materials, the following may be used: the material in the V.A.C.® GRANUFOAM™ Dressing, a molded bed of nails structures, a patterned grid material such as those manufactured by Sercol Industrial Fabrics, 3D textiles such as those manufactured by Baltex of Derby, U.K., a gauze, a flexible channel-containing member, a graft, etc. In some instances, ionic silver may be added to the interface manifold 1420 by, for example, a micro bonding process. Other substances, such as anti-microbial agents, may be added to the interface manifold 1420 as well. In some embodiments, the interface manifold 1420 may comprise a porous, hydrophobic material. The hydrophobic characteristics of the interface manifold 1420 may prevent the interface manifold 1420 from directly absorbing fluid, such as exudate, from the tissue site 1404, but allow the fluid to pass through.

The tissue interface 120 may be prepared for placement with respect to the tissue site 1404, for example, by separating the bridge portions 214, 224 from the respective tissue portions 212, 222 and extending the distal ends 216, 226 of the bridge portions 214, 224 away from the respective tissue portions 212, 222 to a desired distance, for example, as may be dependent upon the location of the tissue site 1404.

The tissue interface 120 may be positioned with respect to the tissue site 1404 such that the tissue portions 212, 222 are positioned at or proximate to the tissue site 1404 and/or the interface manifold 1420 and such that the bridge portions 214, 224 extend away from the tissue site 1404, for example, over peripheral tissue surrounding the tissue site 1404. In this manner, for example, the tissue interface 120 may be in fluid communication with the interface manifold 1420 and/or the tissue site 1404.

A release liner (if included) may be removed to expose the adhesive 1150 and the cover 125 may be applied over the interface manifold 1420, the tissue site 1404, and the optional interface manifold 1420 to provide a fluid seal and a sealed space 1430 between the tissue site 1404 and the cover 125 of the dressing 110. For example, the periphery 1130 of the cover 125 may be positioned in contact with tissue surrounding the tissue site 1404 to provide the sealed space 1430, such that the adhesive 1150 may also be positioned at least between the periphery 1130 of the cover 125 and tissue, such as the epidermis 1406, surrounding the tissue site 1404. The adhesive 1150 may be disposed on a surface of the cover 125 adapted to face the tissue site 1404 such that the adhesive 1150 is effective to seal the cover 125 to various tissue.

The cover 125 may extend over both the tissue portion 212 and the bridge portion 214 and other tissue, such as a portion of the epidermis 1406, surrounding the tissue site 1404 to provide the fluid seal between the cover 125 and the tissue site 1404. For example, the sealed space 1430 may include both the tissue portion 212 and the bridge portion 214 such that fluid may be communicated there-between. In some embodiments, the cover 125 may be positioned over the tissue interface 120 such that the aperture 1175 in the cover 125 and the dressing interface 1170 placed with respect to the aperture 1175 are disposed over the bridge portion 214. As such, the bridge portion 214 may provide at least a portion of a route of fluid communication between the fluid conductor 1165 and the tissue portion 212. In this way, the combination of the tissue portion 212 and the bridge portion 214 may also allow for attachment of the fluid conductor 1165 at a position apart from the tissue site 1404.

With the dressing 110 secured to the patient, the fluid conductor 1165 may be attached to the negative-pressure source 105 and to the dressing interface 1170 to provide a route of fluid communication between the negative-pressure source 105 and the dressing 110. The negative-pressure source 105 may be operated to provide negative-pressure therapy to the tissue site 1404.

Negative pressure applied through the tissue interface 120 can create a negative pressure differential across the fluid restrictions 220 in the fluid management layer 205, which can open or expand the fluid restrictions 220 from their resting state. For example, in some embodiments in which the fluid restrictions 220 may comprise substantially closed fenestrations through the fluid management layer 205, a pressure gradient across the fenestrations or deformation of the fluid management layer 205 can strain the adjacent material of the fluid management layer 205 and increase the dimensions of the fenestrations to allow liquid movement through them, similar to the operation of a duckbill valve. Opening the fluid restrictions 220 can allow exudate and other liquid movement through the fluid restrictions 220 into the manifold layer 210 and the container 115. The fluid management layer 205 can also substantially reduce or prevent exposure of tissue to the manifold layer 210, which can inhibit growth of tissue into the manifold layer 210. If the negative-pressure source 105 is removed or turned-off, the pressure differential across the fluid restrictions 220 can dissipate, allowing the fluid restrictions 220 to move to their resting state and prevent or reduce the rate at which exudate or other liquid from returning to the tissue site through the fluid management layer 205.

Additionally or alternatively, instillation solution or other fluid may be distributed to the dressing 110, which can increase the pressure in the tissue interface 120. The increased pressure in the tissue interface 120 can create a positive pressure differential across the fluid restrictions 220 in the fluid management layer 205, which can open or expand the fluid restrictions 220 from their resting state to allow the instillation solution or other fluid to be distributed to the tissue site 1404.

While shown in a few illustrative embodiments, a person having ordinary skill in the art will recognize that the systems, apparatuses, and methods described herein are susceptible to various changes and modifications that fall within the scope of the appended claims. Moreover, descriptions of various alternatives using terms such as "or" do not require mutual exclusivity unless clearly required by the context, and the indefinite articles "a" or "an" do not limit the subject to a single instance unless clearly required by the context.

Features, elements, and aspects described in the context of some embodiments may also be omitted, combined, or replaced by alternative features serving the same, equivalent, or similar purpose without departing from the scope of the invention defined by the appended claims. For example, one or more of the features of some layers may be combined with features of other layers to provide an equivalent function.

Components may be also be combined or eliminated in various configurations for purposes of sale, manufacture, assembly, or use. For example, in some configurations the container 115 may be eliminated or separated from other components for manufacture or sale. In other example configurations, the controller 130 may also be manufactured, configured, assembled, or sold independently of other components.

The appended claims set forth novel and inventive aspects of the subject matter described above, but the claims may also encompass additional subject matter not specifically recited in detail. Certain features, elements, or aspects may be omitted from the claims if not necessary to distinguish the novel and inventive features from what is already known to a person having ordinary skill in the art.

What is claimed is:

1. A dressing for treating a tissue site with negative pressure, the dressing comprising:
 a manifold layer having a first surface configured to face the tissue site, a second surface opposite the first surface, and a thickness extending between the first surface and the second surface, the manifold layer comprising a tissue portion and a bridge portion, the bridge portion coupled to the tissue portion and comprising a distal end configured to be extended away from the tissue portion by separation of one or more lines of detachment at an edge between the bridge portion and the tissue portion; and
 a flexible drape configured to form a sealed space including the manifold layer at the tissue site;
 wherein the tissue portion and the bridge portion each include a width perpendicular to the edge between the tissue portion and the bridge portion, wherein the width of the tissue portion is greater than the width of the bridge portion, and wherein the tissue portion is free of the lines of detachment.

2. The dressing of claim 1, wherein the lines of detachment are configured to allow the bridge portion to be displaced from a first position with respect to the tissue portion to a second position with respect to the tissue portion.

3. The dressing of claim 2, wherein the one or more lines of detachment comprise at least one slit or at least one perforated line or a combination thereof.

4. The dressing of claim 1, wherein the bridge portion is configured to be rotated with respect to the tissue portion about an axis substantially perpendicular to the first surface and the second surface, wherein the bridge portion is configured to be rotated with respect to the tissue portion about an axis substantially parallel to the first surface and the second surface, or combinations thereof.

5. The dressing of claim 1, wherein, in a first position the bridge portion is disposed adjacent to the edge of the tissue portion, and wherein, in a second position, the bridge portion is further away from the tissue portion than in the first position.

6. The dressing of claim 5, wherein the bridge portion is configured to be rotated about an axis substantially perpendicular to the first surface and the second surface to the second position in which a distal end of the bridge portion is further away from the tissue portion than in the first position.

7. The dressing of claim 5, wherein the bridge portion is configured to be rotated about an axis substantially parallel to the first surface and the second surface to the second position in which a distal end of the bridge portion is further away from the tissue portion than in the first position.

8. The dressing of claim 1, wherein, in a first position the bridge portion at least partially circumscribes the tissue portion.

9. The dressing of claim 8, wherein the bridge portion is configured to be rotated about a plurality of axes substantially perpendicular to the first surface and the second surface to a second position in which the distal end of the bridge portion is further away from the tissue portion than in the first position.

10. The dressing of claim 1, wherein in a first position the bridge portion is disposed adjacent to the edge of the tissue portion and comprises a serpentine pattern.

11. The dressing of claim 10, wherein the bridge portion is configured to be rotated about a plurality of axes substantially perpendicular to the first surface and the second surface to a second position in which the distal end of the bridge portion is further away from the tissue portion than in the first position.

12. The dressing of claim 10, wherein the bridge portion is configured to be rotated about a plurality of axes substantially parallel to the first surface and the second surface to a second position in which the distal end of the bridge portion is further away from the tissue portion than in the first position.

13. The dressing of claim 1, further comprising a first polymeric layer disposed adjacent to the first surface of the manifold layer and comprising a first plurality of fluid restrictive fenestrations extending through the first polymeric layer and configured to deform.

14. The dressing of claim 13, further comprising a second polymeric layer disposed adjacent to the second surface, wherein the second polymeric layer comprises a negative-pressure aperture, wherein the negative-pressure aperture is disposed in the second polymeric layer adjacent to the bridge portion of the manifold layer.

15. The dressing of claim 14, wherein the second polymeric layer comprises a second plurality of fluid restrictive fenestrations extending through the second polymeric layer.

16. The dressing of claim 14, wherein the first polymeric layer is coupled to the second polymeric layer about a periphery of the manifold layer.

17. The dressing of claim 1, wherein the manifold layer comprises an open-cell foam.

18. A system for treating a tissue site, the system comprising:
 a dressing comprising:
  a manifold layer having a first surface configured to face the tissue site, a second surface opposite the first surface, and a thickness extending between the first surface and the second surface, the manifold layer comprising a tissue portion and a bridge portion, the bridge portion coupled to the tissue portion and comprising a distal end configured to he extended away from the tissue portion by separation of one or more lines of detachment at an edge between the bridge portion and the tissue portion; and
  a flexible drape configured to form a sealed space including e manifold layer at the tissue site; and
 a negative-pressure source fluidly coupled to the dressing;
 wherein the tissue portion and the bridge portion each include a width perpendicular to the edge between the tissue portion and the bridge portion, wherein the width of the tissue portion is greater than the width of the bridge portion, and wherein the tissue portion is free of the lines of detachment.

19. The dressing of claim 18, wherein the bridge portion is configured to be rotated with respect to the tissue portion about an axis substantially perpendicular to the first surface and the second surface, wherein the bridge portion is configured to be rotated with respect to the tissue portion about an axis substantially parallel to the first surface and the second surface, or combinations thereof.

20. The dressing of claim 18, wherein, in a first position the bridge portion at least partially circumscribes the tissue portion.

21. The dressing of claim 18, wherein in a first position the bridge portion is disposed adjacent to the edge of the tissue portion and comprises a serpentine pattern.

22. The dressing of claim 18, further comprising a first polymeric layer disposed adjacent to the first surface of the manifold layer and comprising a first plurality of fluid restrictive fenestrations extending through the first polymeric layer and configured to deform.

23. The dressing of claim 22, further comprising a second polymeric layer disposed adjacent to the second surface, wherein the second polymeric layer comprises a negative-pressure aperture configured to provide fluid communication between the manifold layer and the negative-pressure source, wherein the negative-pressure aperture is disposed in the second polymeric layer adjacent to the bridge portion of the manifold layer.

24. The dressing of claim 23, wherein the second polymeric layer comprises a second plurality of fluid restrictive fenestrations extending through the second polymeric layer.

25. The dressing of claim 23, wherein the first polymeric layer is coupled to the second polymeric layer about a periphery of the manifold layer.

26. A method of treating a tissue site with negative pressure, the method comprising:
    extending the bridge portion of the manifold layer of the dressing of claim 1 away from the tissue portion of the dressing;
    positioning the manifold layer with respect to the tissue site such that the tissue portion is adjacent the tissue site and the bridge portion extends away from the tissue site;
    sealing the manifold layer to epidermis adjacent to the tissue site;
    fluidly coupling the dressing to a negative-pressure source via the bridge portion; and
    applying negative pressure from the negative-pressure source to the dressing.

27. The method of claim 26, wherein applying the dressing comprises disposing at least part of the dressing across an edge of the tissue site.

* * * * *